(12) United States Patent
Nachaliel

(10) Patent No.: US 6,928,315 B1
(45) Date of Patent: Aug. 9, 2005

(54) APPARATUS FOR IMPEDANCE IMAGING COUPLED WITH ANOTHER MODALITY

(75) Inventor: Ehud Nachaliel, Lower-Galilee (IL)

(73) Assignee: Mirabel Medical Systems Ltd., Migdal-Haemek (IL)

( * ) Notice: Subject to any disclaimer, the term of this patent is extended or adjusted under 35 U.S.C. 154(b) by 0 days.

(21) Appl. No.: 10/031,761

(22) PCT Filed: May 21, 2000

(86) PCT No.: PCT/IL00/00287

§ 371 (c)(1),
(2), (4) Date: Jan. 18, 2002

(87) PCT Pub. No.: WO01/89379

PCT Pub. Date: Nov. 29, 2001

(51) Int. Cl.[7] ................................................ A61B 5/05
(52) U.S. Cl. ...................................................... 600/407
(58) Field of Search ................................. 600/407–472, 600/547; 382/131, 173, 260; 601/2, 3; 606/42

(56) References Cited

U.S. PATENT DOCUMENTS

| | | |
|---|---|---|
| 3,011,057 A | 11/1961 | Anger |
| 4,291,708 A | 9/1981 | Frei et al. |
| 4,458,694 A | 7/1984 | Sollish et al. |
| 4,763,660 A | 8/1988 | Kroll et al. |
| 5,299,253 A | 3/1994 | Wessels |
| 5,688,486 A | 11/1997 | Watson et al. |
| 5,733,525 A | 3/1998 | Klaveness |
| 5,810,742 A | 9/1998 | Pearlman |
| 6,157,697 A | 12/2000 | Mertelmeier et al. |

FOREIGN PATENT DOCUMENTS

| | | |
|---|---|---|
| EP | 0 945 103 | 9/1999 |
| EP | 1 000 580 | 5/2000 |
| WO | WO 98/46276 | 10/1998 |
| WO | WO 99/12470 | 3/1999 |
| WO | WO 99/12577 | 3/1999 |
| WO | WO 01/64102 | 9/2001 |

OTHER PUBLICATIONS

Watanabe, R. et al.; "CT Analysis of the Use of the Electrical Impedance Technique to Estimate Local Oedema in the Extremities in Patients with Lymphatic Obstruction;" 1998; pp. 60-65; Medical and Biological Engineering and Computing, GB, Peter Peregrinus Ltd. Stevenage; vol. 36; No. 1; XP000727970.

Piperno, G. et al.; "Breast Cancer Screening by Impedance Measurements;" 1990; pp. 111-117; Frontiers Med. Biol. Engng; vol. 2; No. 2.

Frerichs, I. et al.; "Electrical Impedance Tomography in Monitoring Experimental Lung Injury;" 1998; pp. 829-836; Intensive Care Medicine; vol. 24; XP002180964.

*Primary Examiner*—Ali Imam
(74) *Attorney, Agent, or Firm*—Fenster & Company

(57) ABSTRACT

Multi-element impedance probe apparatus (40), adapted to produce an image of a body tissue, having a structure, comprising: a raster of sensors (43), comprised of a substantially radiolucent, conductive material; substantially radiolucent conductive wiring (44), forming conductive connections with the sensors; and a substantially radiolucent substrate (46), on which the sensors are mounted.

29 Claims, 13 Drawing Sheets

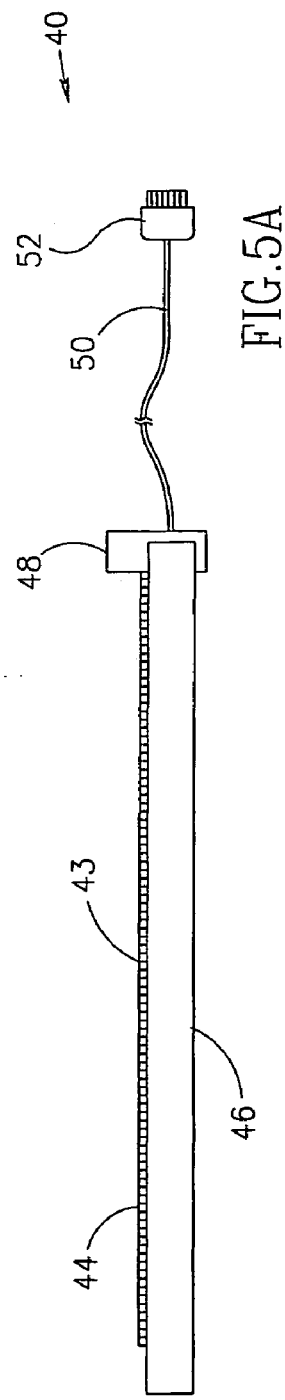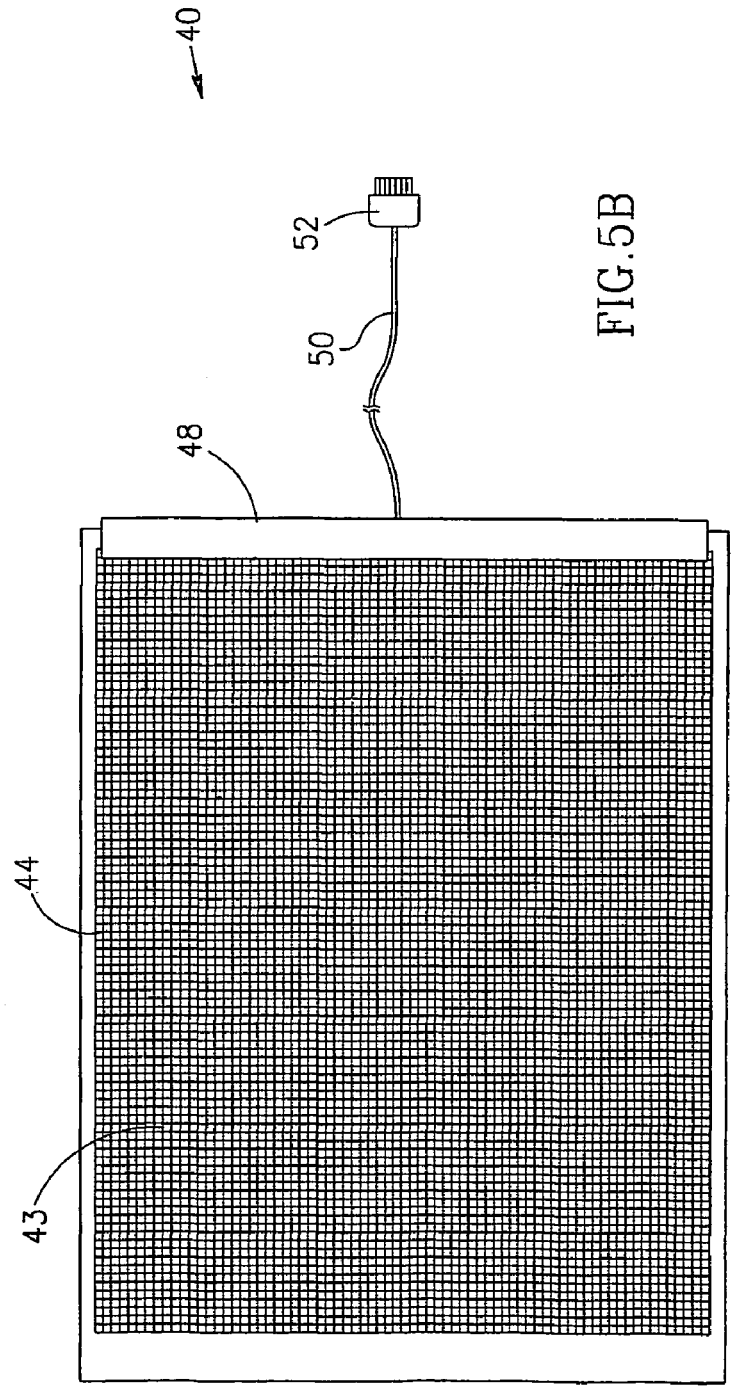

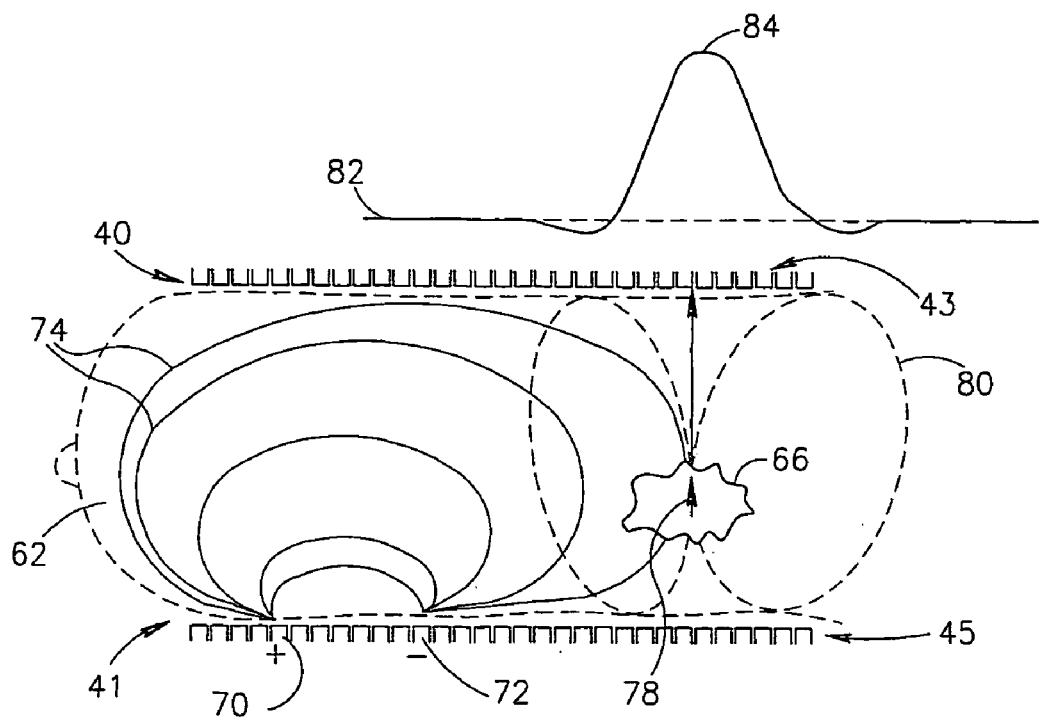
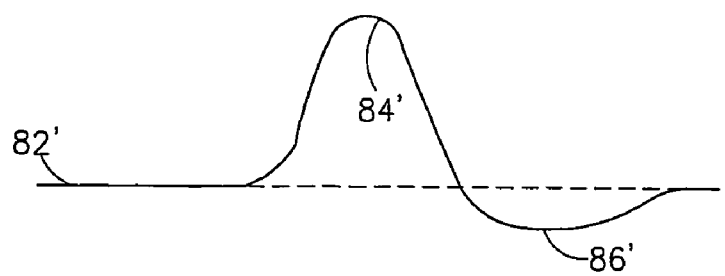
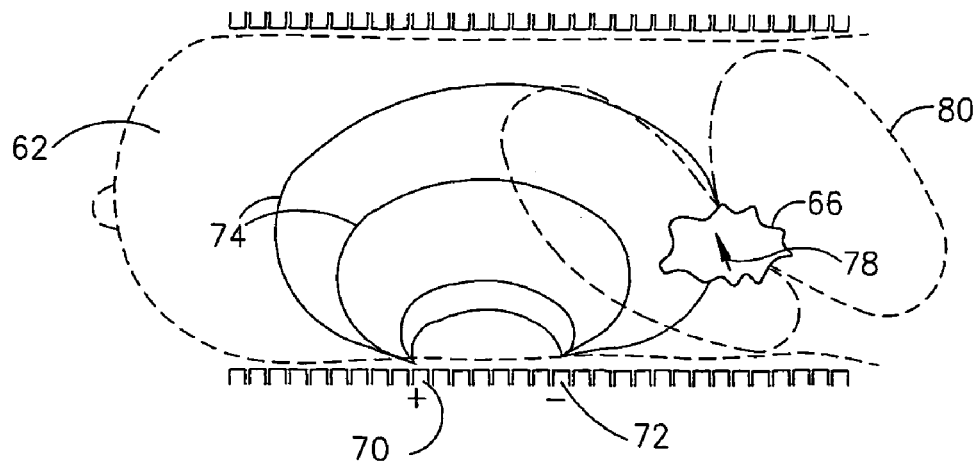
FIG.7A
FIG.7B

APPARATUS FOR IMPEDANCE IMAGING COUPLED WITH ANOTHER MODALITY

RELATED APPLICATIONS

This application is a U.S. national filing of PCT Application No. PCT/IL00/00287, filed May 21, 2000, the disclosure of which is incorporated herein by reference.

FIELD OF THE INVENTION

The present invention relates generally to medical imaging techniques. In particular the present invention relates to performing impedance imaging in conjunction with any of the various forms of x-ray imaging or nuclear imaging.

BACKGROUND OF THE INVENTION

In Conventional x-ray radiography, x-rays from a nearly point source are directed on the part of the body (organ) to be imaged. The x-rays emerging from the organ are detected to form a two-dimensional image, producing a shadowgram of the part of the body being imaged. The points on the image have a brightness related to the intensity of the x-rays at that point. Image production relies on the fact that different parts of the anatomy absorb different amounts of x-rays. At times, it is necessary to enhance the x-ray absorption of an organ by introducing x-ray absorbers to the body. Examples of x-ray contrast agents are physiologically acceptable organic salts, especially those containing one or more tri-iodo groups in their structure, like 3-acetylamino-2,4,6-triiodobenzoic acid, and 5-[(3-amino-2,4,6-triiodophenyl) methylamino]-5-oxypentanoic acid.

Mammography is a procedure which utilizes x-ray imaging for the examination of the breast. It is used for the detection and diagnosis of breast cancer, for preoperative localization of suspected lesions and for guiding biopsy needles.

A schematic representation of a mammogram 10 is shown in FIG. 1. Generally, mammogram 10 comprises a head 12 and a base 16. Head 12 comprises an x-ray tube 14. Base 16 comprises three parts:
1. A support plate 22 on which the breast rests;
2. A compression plate 20 mounted on a gantry 21 above support plate 22, for compressing the breast firmly against support plate 22; and
3. An image receptor 18, positioned directly below support plate 22. In digital mammography, image receptor 18 is an electronic detector connected to a computer 24.

X-ray imaging involves placing the breast (not shown) on support plate 22, bringing compression plate 20 down for firm compression of the breast and activating x-ray tube 14. Rays transmitted through the breast strike image receptor 18 where they interact and deposit energy locally, forming an image.

A schematic representation of stereoscopic mammography is shown in FIG. 2. In stereoscopic mammography, head 12, is mounted on a gantry (not shown) that turns on an arc about base 16. As a result, x-ray images can be obtained from different angular views. Images from different angular views can be used to generate a three dimensional location of a suspected lesion.

Mammogram 10 is shown upright, for use with patients that are sitting or standing. Generally, its assembly, including support plate 22 and compression plate 20, can be rotated so as to obtain x-ray measurements when the patient is lying down. Generally, the assembly of mammogram 10, including x-ray tube 12, support plate 22 and compression plate 20 may be rotated at any angle about the horizontal axis, so as to obtain images of the breast from any desired position.

Stereotactic biopsy is a procedure that utilizes stereoscopic mammography for guiding a biopsy needle to the location of a suspected lesion. A core sample tissue is then cut for laboratory examination.

A stereotactic biopsy system comprises a stereoscopic mammogram which has a secondary gantry for positioning a biopsy needle. Typically, the secondary gantry is capable of moving along all axes and in at least one rotational direction. However, a gantry having fewer degrees of freedom may also be used. The secondary gantry is equipped with a spring-loaded biopsy needle which serves as a cutting and collecting device.

Computed tomographic images are cross-sectional images of internal structures of the body, as reconstructed from a large number of measurements of x-ray transmission through a patient, acquired from different views around the patient. The diagnostic CT scanner comprises an x-ray tube with collimation to provide the slice thickness, a linear array of detector elements and a reconstruction computer. Typically, the x-ray tube and the detectors are on a rotating gantry.

In nuclear imaging, a radioactive isotope is injected to, inhaled by or ingested by a patient. The isotope, provided as a radioactive-labeled pharmaceutical (radio-pharmaceutical) is chosen based on bio-kinetic properties that cause preferential uptake by different tissues. The gamma photons emitted by the radio-pharmaceutical are detected by radiation detectors outside the body, giving its spatial and uptake distribution within the body, with little trauma to the patient. Examples of radio-pharmaceuticals used in nuclear medicine are [$^{90}$Tc]-MIBI and [$^{125}$I]-albumin.

The basic nuclear-imaging detector is an Anger-type scintillation camera, as disclosed in U.S. Pat. No. 3,011,057, incorporated herein by reference. In practice, more advanced units of this general type are used. Generally, an Anger type camera comprises:
  a scintillation crystal (generally, a doped NaI(Tl) crystal).
  an array of photodetectors (generally, photo-multiplier tubes, PMTs), to give positional sensitivity; and
  coordinate computation circuitry, CCC.

Each photodetector has an x and a y coordinate. When a photon is absorbed by the scintillation crystal, light is generated at the point of absorption. Several photodetectors receive the light and produce signals. The normalized X' and Y' coordinates of the light event are determined by the strength of the signals generated by each photodetector. The total energy of the light event, proportional to the sum of all the signals, is represented by the Z pulse. Only Z pulses within a given range are counted. Other types of gamma cameras are also widely used.

SPECT (Single-Photon-Emission Computed Tomography) is based on conventional nuclear imaging technique coupled with tomographic reconstruction methods, wherein projection (or planar) data of single photons acquired from different views around the tissue are reconstructed, to generate cross-sectional images of the internally distributed radio-pharmaceuticals. SPECT images provide enhanced contrast, when compared with planer images obtained with conventional nuclear imaging methods.

A typical SPECT system consists of a single or multiple radiation detectors arranged in a specific geometric configuration and a mechanism for moving the radiation detectors around the tissue to acquire data from different projection views.

PET (Positron Emission Tomography) uses as radiopharmaceuticals biological molecules that carry a positron-emitting isotope (e.g., $^{11}$C, $^{13}$N, $^{15}$O, $^{18}$F, $^{52}$Fe). Within a short period (a few minutes), the isotope accumulates in the area of the body for which the molecule has an affinity. For example, glucose labeled with $^{11}$C accumulates in tumors where it is used as a source of energy. The radioactive nuclei decay by positron emission, and the ejected positron combines with an electron almost instantaneously. The two particles undergo annihilation and their combined mass of 1.022 MeV is divided between two 0.511 MeV photons that fly away in opposite directions from one another. PET is based on the coincident (simultaneous) detection, by two opposite detectors, of two 0.511 MeV photons. The source of the photons is along the line connecting them. Data acquired from different views around the tissue are reconstructed, using one of various known image reconstruction methods, to generate cross-sectional images of the internally distributed positron-emitting isotope.

A typical PET system consists of at least one pair of radiation detectors situated opposite to each other and a mechanism for moving the radiation detectors around the tissue to acquire data from various projection views.

Impedance imaging is a procedure which relies on variations in electrical impedance of tissue as suggestive of the possibilities of lesions. U.S. Pat. Nos. 4,291,708 and 4,458,694 and the article, "Breast Cancer Screening by Impedance Measurements," by G. Piperno et al., Frontiers Med. Biol. Eng., Vol. 2 pp. 111–117, the disclosures of which are incorporated herein by reference, describe systems for determining the impedance between a point of the surface of the tissue and some reference point on the body of the patient. With the use of a multi-element impedance probe, an impedance image of a tissue such as a breast can be generated and used for the detection of tumors, especially malignant tumors.

The multi-element impedance probe may be constructed as a series of flat, conducting, sensing elements, mounted onto a PVC base or some other flexible, nonconductive substrate. A lead wire is connected between each of these elements and detector circuitry. Impedance measurements between the elements and an electrode attached to a remote part of the body are used to determine impedance variations in the tissue, using signal processing circuitry. Alternatively, two multi-element impedance probes may be used, and impedance measurements between them are used to determine impedance variations in the tissue.

In general, impedance imaging involves the following procedure:
1. A reference electrode is held by the patient (or attached to some part of her body);
2. A multi-element impedance probe is placed on the tissue whose impedance is to be imaged;
3. A signal is applied via the reference electrode; and
4. The resulting current (or voltage) response across the tissue is measured by each sensor of the multi-element impedance probe and fed to an electrical impedance scanning device which generates an impedance image.

U.S. Pat. No. 5,810,742, "Tissue Characterization Based on Impedance Images and on Impedance Measurements," the disclosure of which is incorporated herein by reference, describes a multi-element impedance probe for the identification of tissue type from impedance images. U.S. Pat. No. 5,810,742 also describes mammography systems utilizing two or more probe arrays on the breast. PCT application PCT/IL00/00127, entitled "uniform, Disposable Interface for Multi-Element Probe," filed Mar. 1, 2000, the disclosure of which is incorporated herein by reference, describes an interface sheet or other structure to be used in conjunction with a multi-element impedance probe.

U.S. patent application Ser. No. 09/460,699, now U.S. Pat. No. 6,560,480, entitled "Location of Anomolies in Tissue and Guidance of Invasive Tools Based on Impedance Imaging", the disclosure of which is incorporated herein by reference, describes impedance imaging methods for determining the depth of a lesion within an organ of a patient. The position of an anomaly, including its depth, may be determined from a plurality of impedance maps, obtained by systematically mapping the surface of the organ. Alternatively, two multi-element impedance probes are used, one serving as an exciting electrode, producing electrifying signals, the other serving as a passive sensor, wherein the first impedance probe produces a dipole in the organ. The characteristics of the dipole around the anomaly are indicative of the distance from the source of the dipole to the anomaly. Sometimes, a minimally invasive tool—an impedance-guided biopsy needle, is used, together with an external, sensing probe. As the impedance-guided biopsy needle approaches a lesion, it generates an electrifying signal. Since the lesion's response to the electrifying signal is different from that of the surrounding tissue, the image formed by the sensing, external probe can be used to monitor, manually or automatically, the movements of the impedance-guided biopsy needle toward the lesion. When the needle touches or enters the lesion, the direct electrification of the lesion by the needle induces a detectable change in the signals due to the lesion, which serves to confirm that the needle has indeed reached the lesion, whereupon, a core sample is taken.

Contrast agents are compounds that may be administered to the patient to enhance the contrast between a particular organ of interest and the surrounding tissue. Contrast agents are sometimes used with x-ray imaging, with MRI, and may also be used with impedance imaging. U.S. Pat. No. 5,733,525, whose disclosure is incorporated herein by reference, provides a comprehensive list of contrast agents suitable for impedance imaging, many of them are also useful as x-ray contrast agents. Examples are the aforementioned physiologically acceptable organic salts containing one or more tri-iodo groups in their structure. Other examples, suitable for impedance imaging but not suitable for x-ray imaging, are complexed paramagnetic metal ions such as Fe, Cr and Mn.

To minimize the uncertainty in deciphering the results of any imaging procedure (modality), it is sometimes desirous to compare results of the different modality and seek agreement between them. However, spatial registration may be a problem in the superposition of the images. This is especially true with regard to soft tissue, such as a breast. The breast can change its shape and orientation between imaging sessions. If one conducted a mammography of the breast, using mammogram, and an impedance measurement of the breast moments later, on some other apparatus, it would be very difficult to compare the results exactly; a lesion, if it existed, would be likely to move relative to the imagers, between procedures. Coincident spatial registration is also useful in the guiding of a biopsy needle for core sampling.

SUMMARY OF THE INVENTION

An aspect of some embodiments of the invention relates to a method of using two imaging procedures (modalities), namely, impedance imaging and a second modality, referenced to a same reference indicator, in order to enhance lesion identification in humans and animals.

In an embodiment of the invention, the second modality is any of the various known forms of x-ray imaging or nuclear imaging.

In some embodiments of the invention, the second modality is performed before, after, or simultaneously with the impedance imaging while the impedance probe remains in place. Alternatively, the impedance probe is removed, but the reference indicator remains in place and body part remains referenced to the reference indicator.

An aspect of some embodiments of the invention relates to dual-purpose apparatus for impedance imaging and a second modality, referenced to a same reference indicator.

In an exemplary embodiment of the invention, impedance imaging is conducted with a multi-element impedance probe. In an embodiment of the invention, the impedance probe is positioned on or attached to a structure of the second modality, as an integral unit, or as modules that connect with each other with positive placement of position. Alternatively, the impedance probe is positioned on or attached to the tissue to be examined.

In an embodiment of the invention, the reference indicator is comprised in a structure that is common to the two imagers. Precise, repeatable alignment of the impedance probe within the second modality may be achieved by at least one mechanical guide such as a groove, a bracket, a stop, a straight edge, a rim, or a similar means, thus insuring good spatial coincidence. Alternatively, the reference indicator is comprised in an alignment mark associated with the impedance probe and visible on the image of the second modality. Optionally, the alignment mark is also visible to the eye. Alternatively, the location of the alignment mark with respect to the impedance probe is known.

However, it should be noted that while it is desirable, in many cases, to align the coordinate systems of the impedance image and the other image using some external means such as alignment marks or mechanical means, such means are not absolutely necessary. In general, it is possible to align the images by overlaying them and matching characteristic structures in both images, such as the edge of the breast. Also, simultaneous application of the two alignment techniques is a solution to the alignment problem.

An aspect of some embodiments of the invention relates to a method of superimposing the images of impedance imaging and the second modality for analysis and comparison.

Optionally, images obtained from either modality are digital and are displayed on a computer monitor, where they can be superimposed and aligned with each other.

Alternatively, the x-ray or nuclear image is produced on film, and the impedance image, which is generally digital, is printed from the computer onto a transparency, so that the two images can be superimposed and viewed together on a light box.

Alternatively still, a non-digital x-ray or nuclear image is scanned and viewed on a computer monitor, together with the impedance image.

In some embodiments of the invention, where the images are digital and displayed on a computer monitor, image processing may be performed. It may include dimensional expansion or reduction of one image, in order to match the dimensions of the other image, zooming in on a feature, the removal of noise and other known image processing techniques.

An aspect of some embodiments of the invention relates to a radiolucent impedance probe for the dual-purpose apparatus. The impedance probe of this aspect is generally transparent to x-rays and gamma rays and does not interfere with the second modality.

In some embodiments of the invention, the impedance probe comprises conductive sensors and wiring of a radiolucent conductive material such as graphite-based deposits or thin layers of aluminum-based deposits. The impedance probe may comprise a substrate of a radiolucent, nonconductive material such as plastic (for example, Mylar®, polycarbonate, PVC, or Tyvec®) or paper. The substrate may be hypoallergenic and otherwise biocompatible. Optionally, the impedance probe is completely transparent to x-rays and gamma rays.

An aspect of some embodiments of the invention relates to a partially radiolucent impedance probe for the dual-purpose apparatus. The impedance probe is partially transparent to x-rays and gamma rays, causing only minimal shadowing. Optionally, signal processing is used to remove the known shadow pattern of the impedance probe from the x-ray or nuclear images.

An aspect of some embodiments of the invention relates to an interface sheet, interfacing between the tissue and the impedance probe of the dual-purpose apparatus.

Optionally, the interface sheet is disposable and sterile (while the impedance probe itself is reusable).

Optionally, the interface sheet is made of hydrogel (for example, TanGel, containing between 70% and 95% water, by weight, and having conductivity comparable to that of the tissue) thus providing good wetting of the body tissue, thereby eliminating the need to spread a gel over the patient, and eliminating the unpleasantness to the patient, associated with the gel. Optionally, the interface sheet is transparent or partially transparent to x-rays and gamma rays, so as to cause little interference to x-ray and nuclear imaging.

An aspect of some embodiments of the invention relates to utilizing x-ray imaging as the second modality together with impedance imaging.

An aspect of some embodiments of the invention relates to providing precise, repeatable alignment of the impedance image within the x-ray image using an x-ray absorbing alignment mark on the otherwise radiolucent or partially radiolucent impedance probe. Optimally, the x-ray absorbing alignment mark is of a material that is sufficiently absorbing to show on the x-ray image, but not so absorbing that it can cause artifacts, for example, aluminum. Optionally, the x-ray absorbing alignment mark comprises at least two or three lines of x-ray absorbing material, which may be arranged so as to provide at least one and preferably two junctions. The x-ray absorbing lines may be visible. Alternatively, their locations on the impedance probe are known. In some embodiments of the invention, x-ray imaging is performed with the impedance probe in place.

An aspect of some embodiments of the invention relates to the use of x-ray mammography as the second modality. The mammogram may be stereoscopic. X-ray imaging may be performed from one, two or more viewing angles.

In some embodiments of the invention, a single, preferably, a multi-element, impedance probe is placed on the tissue side of the compression plate, or on the tissue side of the support plate of the mammogram. Alternatively, a multi-element probe is comprised in one of the plates. An electrical signal is applied via a separate reference electrode held in the patient's hand or attached to some part of the patient's body, such as an arm, a back, or a leg.

Alternatively, two impedance probes, at least one of which is preferably a multi-element impedance probe, are used. One is placed on the tissue side of the compression plate of the mammogram. The other is placed on the tissue side of the support plate. Alternatively, the two impedance probes are comprised in the two plates. The impedance probes are used alternately or simultaneously. One probe, which may be a conducting plate, serves as an electrifying source and the other, a multi-element probe, serves as a sensor.

Optionally, the tissue on which tests are performed is held under compression by the compression plate throughout the two procedures: x-ray imaging and impedance imaging. This prevents movement of the soft breast tissue between procedures and enables comparison of the results.

An aspect of some embodiments of the invention relates to multi-purpose apparatus for x-ray mammography, impedance imaging and biopsy core sampling, using a single reference indicator for the three procedures.

The 3-D location of a suspected lesion, for guiding the biopsy needle, may be determined from stereoscopic x-ray imaging together with a 2-D impedance map.

Alternatively, where the x-ray imaging fails to show a suspicious signal, but such a signal is observed on the 2-D impedance map, two multi-element impedance probes are used to apply and sense a dipole over the breast in order to determine the suspected lesion 3-D location. An impedance-guided biopsy needle may be used to reach the location of the suspected lesion and take a core sample.

An aspect of some embodiments of the invention relates to the use of CT as the second modality.

In an embodiment of the invention, with the patient lying on an examination table, an impedance probe is attached to the body portion to be impedance imaged and impedance imaging is performed. Alternatively, an impedance probe is attached to the table, under the patient. Preferably, the impedance probe is radiolucent. The radiolucent impedance probe may have an alignment mark, for example, a rim of x-ray absorbing material (preferably only partially absorbing), around its circumference and CT measurements are performed with the radiolucent impedance probe in place. In this manner, an outline of the 2-D impedance probe is produced on the CT image, and comparison of the two images is possible.

Alternatively, the impedance probe is not radiolucent and comprises any known impedance probe that has been fitted with a detachable mount of at least partially x-ray absorbing material. The mount is attached to the patient (for example by straps) or to the table under the patient, the impedance probe is inserted into the mount and impedance imaging is performed. The impedance probe is then removed from the mount which remains in place for defining the field of view of the impedance image on the CT image.

An aspect of some embodiments of the invention relates to using nuclear imaging as the second modality. In some embodiments of the invention, the dual-purpose apparatus comprises a gamma camera (which may be hand-held) and an impedance probe.

Preferably, the patient is motionless while impedance imaging is performed.

An aspect of some embodiments of the invention relates to a method of providing precise, repeatable alignment of the impedance image within the nuclear image of the gamma camera with a radioactive alignment mark.

The impedance probe may be radiolucent and comprise a radioactive alignment mark of a γ-emitting radioactive deposit. Alternatively, a radioactive alignment mark such as an outline of the impedance probe is traced with a brush on a surface against which the probe is positioned. This may be a tissue surface or a structural surface such as a support plate or an examination table.

Alternatively still, the gamma camera is provided with a probe-holding fixture which places an impedance probe directly in the field of view of the camera, a specific distance from it. The impedance probe is placed in the fixture, pressed against the patient, and an impedance image is taken. The impedance probe is then removed and a nuclear image of the same field of view is taken without moving the camera. Alternatively, if the impedance probe is radiolucent, a nuclear image may be taken with the impedance probe in place.

An aspect of some embodiments of the invention relates to a method of using three imaging procedures, namely, impedance imaging, mammography and gamma scanning, referenced to a same reference indicator. The impedance probe may be radiolucent and comprised in the compression plate of the mammogram. Optionally, after mammography and impedance imaging are conducted, a gamma camera is attached onto the compression plate-impedance probe, using a special fixture, for example, special end-brackets, and gamma scanning is conducted. Optionally, the tissue remains under compression throughout the procedure.

An aspect of some embodiments of the invention relates to using of SPECT or PET as the second modality.

As in the case of the CT, the patient may lay on a SPECT or PET table, and an impedance probe is attached to the patient or to the table under the table. As in the case of gamma-ray imaging, the impedance probe may be radiolucent and comprises a radioactive alignment mark (of an isotope which emits γ rays or of an isotope which emits pairs of positrons) on the probe, or traced on a surface against which the probe is positioned.

An aspect of some embodiments of the invention relates to a method of administering dual-purpose contrast agents which enhance desired features on images of the two modalities — impedance imaging and x-ray imaging. Examples of contrast agents suitable for x-ray imaging and impedance imaging are iodinated contrast agents, containing one or more groups of tri-iodo, like 3-acetylamino-2,4,6-triiodobenzoic acid, and 5-[(3-amino-2,4,6-triiodophenyl)methylamino]-5-oxypentanoic acid. Further examples of such dual purpose contrast agents are disclosed in U.S. Pat. No. 5,733,525, the disclosure of which is incorporated by reference.

Apart from the inherent simplicity of the method, the potential advantages of using a single contrast agent for two modalities include one or both of:

i. the uptake of the agent is the same for the two modalities; therefore, the shape or form of the feature under examination will be similar on the images of the two modalities; and ii. the risk of interaction between two agents, each administered for a different modality, is eliminated.

In some embodiments of the invention, the required dose is the same for the two modalities. The contrast agent is administered, and the two modalities are performed, in any order, within the required period of the contrast agent performance.

Alternatively, one modality requires a lower dose of the contrast agent than the other. In such cases, the lower dose is administered, and the modality associated with it is performed first. A second dose, making up the difference between the doses, is then administered, and the second modality is performed.

In some embodiments of the invention, the radio-pharmaceutical contrast agent is a known impedance contrast agent, made with radioactive isotopes. For example, for gamma cameras or SPECT with impedance imaging, the aforementioned iodinated contrast agents containing the tri-iodo group, with $^{123}$I, $^{125}$I or $^{131}$I in place of the stable iodine, may be used. For PET and impedance imaging, physiologically acceptable organic salts (such as the aforementioned salts) with positron emitters $^{11}$C, $^{13}$N and $^{15}$O in place of the stable C, N and O in the organic molecule, may be used. Alternatively, complexed paramagnetic iron ions with $^{52}$Fe isotope may be used.

An aspect of some embodiments of the invention relates to a method administering a radio-pharmaceutical that is also a contrast agent for impedance imaging.

In some preferred embodiments of the invention, the required dose of the is radio-pharmaceutical is substantially the same as the required dose of the impedance contrast agent. The radioactive contrast agent is administered, and the two modalities are performed—the nuclear at the required time from the administration, and the impedance imaging, before or after it.

Alternatively, the nuclear imaging requires a lower dose. The low dose of the radioactive agent is administered, and the nuclear imaging performed. A stable agent of the same composition is administered as the second stage, and the impedance imaging performed.

An aspect of some embodiments of the invention relates to triple-purpose agents that serve as radio-pharmaceutical for nuclear imaging and as contrast agents both for impedance imaging and x-ray imaging. The aforementioned iodinated contrast agents containing the tri-iodo group, with $^{123}$I, $^{125}$I or $^{131}$I in place of the stable iodine, may be used.

There is thus provided, in accordance with an embodiment of the invention, Multi-element impedance probe apparatus, adapted to produce an image of a body tissue, having a structure, comprising:

a raster of sensors, comprised of a substantially radiolucent, conductive material;

substantially radiolucent conductive wiring, forming conductive connections with the sensors; and a substantially radiolucent substrate, on which the sensors are mounted.

Optionally, the apparatus comprises two impedance probes which operate in tandem, one acting as an electrifying source and the other as a sensor.

Optionally, the apparatus includes a conductive layered structure, covering the surface of the probe and suitable for providing an interface between the probe and the tissue. Optionally, the structure comprises a material having conductivity substantially similar to the conductivity of the tissue. Optionally, the structure is radiolucent.

In an embodiment of the invention, the impedance probe comprises an aligning feature. Optionally, the aligning feature comprises at least one alignment mark that is opaque to x-rays. Optionally, the aligning feature comprises at least one alignment mark that emits γ rays. Optionally, the aligning feature comprises at least one alignment mark that emits pairs of positrons. Optionally, the aligning feature comprises at least two lines, a substantial distance apart with respect to the size of the impedance probe. Optionally, the aligning feature comprises at least two intersections, a substantial distance apart with respect to the size of the impedance probe. Optionally, the aligning feature comprises an outline of the probe painted on a surface against which the impedance probe is positioned. Optionally, the aligning feature comprises a detachable mount to which the impedance probe is attached during operation thereof.

there is further provided, in accordance with an embodiment of the invention, apparatus for tissue examination comprising:

an impedance imager comprising at least one impedance probe with a first field of view and adapted to produce an impedance image of a body tissue, referenced to a reference indicator; and at least one additional imager of a modality different from impedance imaging, having a second field of view, at least partially common to the first field of view, and adapted to produce an image of body tissue, referenced to the reference indicator.

Optionally, the impedance imager comprises probe apparatus according as defined above. Optionally, the reference indicator is comprised in a structure that provides positioning of at least one of the imagers. Optionally, the impedance imager and the at least one additional imager form an integral unit.

Optionally, the impedance imager is a first module and each additional imager is an additional module, wherein the modules may be used independently or together.

The apparatus optionally includes a processing unit common to the impedance imager and the at least one additional imager for processing the images. Optionally, the apparatus includes a display unit common to the impedance imager and the at least one additional imager, wherein the display unit is operative to selectively display each image individually or the images superimposed. Optionally, the apparatus includes a control panel common to the impedance imager and the at least one additional imager. Optionally, the apparatus includes a biopsy device, adapted to perform biopsy on the tissue.

In an embodiment of the invention, the at least one additional imager comprises an x-ray imager. In an embodiment of the invention, the at least one additional imager comprises a mammogram comprising:

an x-ray tube, which produces a beam of x-rays;

a support plate, adapted to support the tissue when it is irradiated by the x-ray tube;

an x-ray image receptor, associated with the support plate and adapted to produce an x-ray image of the tissue, wherein the at least one impedance probe is located between the x-ray tube and the x-ray image receptor.

There is further provided, in accordance with an embodiment of the invention, apparatus for x-ray mammography and impedance imaging, comprising:

an x-ray tube, which produces a beam of x-rays;

a support plate, adapted to support a soft body tissue when it is irradiated by the x-ray tube;

an x-ray image receptor, associated with the support plate and adapted to produce an x-ray image of the tissue, referenced to a reference indicator;

an impedance imager, comprising at least one impedance probe, located between the x-ray tube and the x-ray image receptor, having a field of view that is at least partially common to a field of view of the x-ray tube and adapted to produce an image of body tissue, referenced to the reference indicator.

Optionally, the apparatus includes a compression plate, adapted to travel between the x-ray tube and the support plate and to provide compression against the tissue. Optionally, the at least one impedance probe is comprised in the compression plate.

Additionally or alternatively, the at least one additional imager may comprise a CT imager. Additionally or alternatively the apparatus may include a gamma camera, having a field of view that is at least partially common to a field of view of the at least one impedance probe, wherein the gamma camera is adapted to produce a gamma-ray image of the tissue, referenced to the reference indicator. Additionally or alternatively, the at least one additional imager may comprise a gamma camera. Optionally, the at least one impedance probe is attached to the gamma camera with a fixed mechanical attachment, in a field of view of the gamma camera, at a specific distance from the gamma camera.

Additionally or alternatively, the at least one additional imager may comprise a SPECT imager or a PET imager.

Optionally, the tissue is human tissue.

There is further provided, in accordance with an embodiment of the invention, a composition of matter that is a physiologically acceptable organic salt which is both an agent that enhances impedance imaging and a radio-pharmaceutical agent.

Optionally, the composition is also an agent that enhances x-ray imaging. Optionally, the radio-pharmaceutical agent emits gamma rays. Optionally, the radio-pharmaceutical agent emits positron pairs.

In an embodiment of the invention, the radio-pharmaceutical agent is selected from a tri-iodo group in which a stable iodine isotope is replaced by a radioactive iodine isotope.

In an embodiment of the invention, the radio-pharmaceutical agent is selected from a tri-iodo group in which any of stable C, O and N isotopes are replaced with any of positron emitting $^{11}$C, $^{15}$O and $^{13}$N isotopes.

In an embodiment of the invention, the radio-pharmaceutical agent is a paramagnetic iron ion wherein the stable iron isotope is replaced by $^{52}$Fe isotope.

There is further provided, in accordance with an embodiment of the invention a method of imaging a body tissue by an impedance imager and by an additional imager of a modality different from impedance imaging, comprising:

positioning an impedance probe of an impedance imager so that at least a portion of a field of view of the impedance probe is common with at least a portion of a field of view of the additional imager;

acquiring an impedance image, referenced to a reference indicator; and acquiring an image of the additional imager, referenced to the reference indicator.

Optionally, acquiring an impedance image comprises acquiring an impedance image with apparatus as defined above.

Optionally, positioning comprises attaching to a structure of the additional imager. Alternatively, positioning comprises attaching to the body tissue.

In an embodiment of the invention, the method includes removing the impedance probe before acquiring the image of the additional imager. Optionally, comprises removing by sliding, without substantially moving or disturbing the tissue.

Optionally the method includes:

acquiring an impedance image comprises acquiring an impedance image with apparatus according to apparatus defined above wherein the aligning feature comprises a detachable mount to which the impedance probe is attached during operation thereof; and removing comprises removing the impedance probe from the detachable mount, while leaving the detachable mount in place.

Optionally, acquiring an image of the additional imager comprises acquiring an x-ray image, which may be, for example, a mammography image. Alternatively or additionally acquiring an image of the additional imager may comprise acquiring an x-ray CT image. In an embodiment of the invention, the method includes administering a dual-purpose contrast agent, effective for enhancing the contrast of a desired feature both on the x-ray image and on the impedance image.

Alternatively or additionally acquiring an image of the additional imager may comprise acquiring a SPECT or PET image.

Additionally or alternatively, the method may include acquiring a gamma-ray image, referenced to the reference indicator.

Additionally or alternatively, acquiring an image of the additional imager may comprise acquiring a gamma-ray image.

Optionally, the method includes administering a contrast agent which is a composition of matter in accordance with any of the materials defined above.

Optionally, the method includes performing a biopsy on the tissue utilizing a biopsy needle. Optionally, the biopsy needle is an impedance-guided biopsy needle. Optionally, the biopsy is performed under guidance of impedance images acquired during insertion and positioning of the biopsy needle.

BRIEF DESCRIPTION OF THE DRAWINGS

A description of exemplary embodiments of the invention follows. The description should be read together with the attached drawings, in which same number designations are maintained throughout the figures for each element and in which:

FIG. 5A is a schematic illustration of a side view the multi-element impedance probe, in accordance with an embodiment of the present invention;

FIG. 5B is a schematic illustration of a top view of the multi-element impedance probe, in accordance with an embodiment of the present invention;

FIGS. 7A–7C are schematic illustrations of a method of depth determination of the multi purpose apparatus, using impedance imaging to form a dipole, in accordance with an embodiment of the present invention;

DETAILED DESCRIPTION OF PREFERRED EMBODIMENTS

Figure 1:
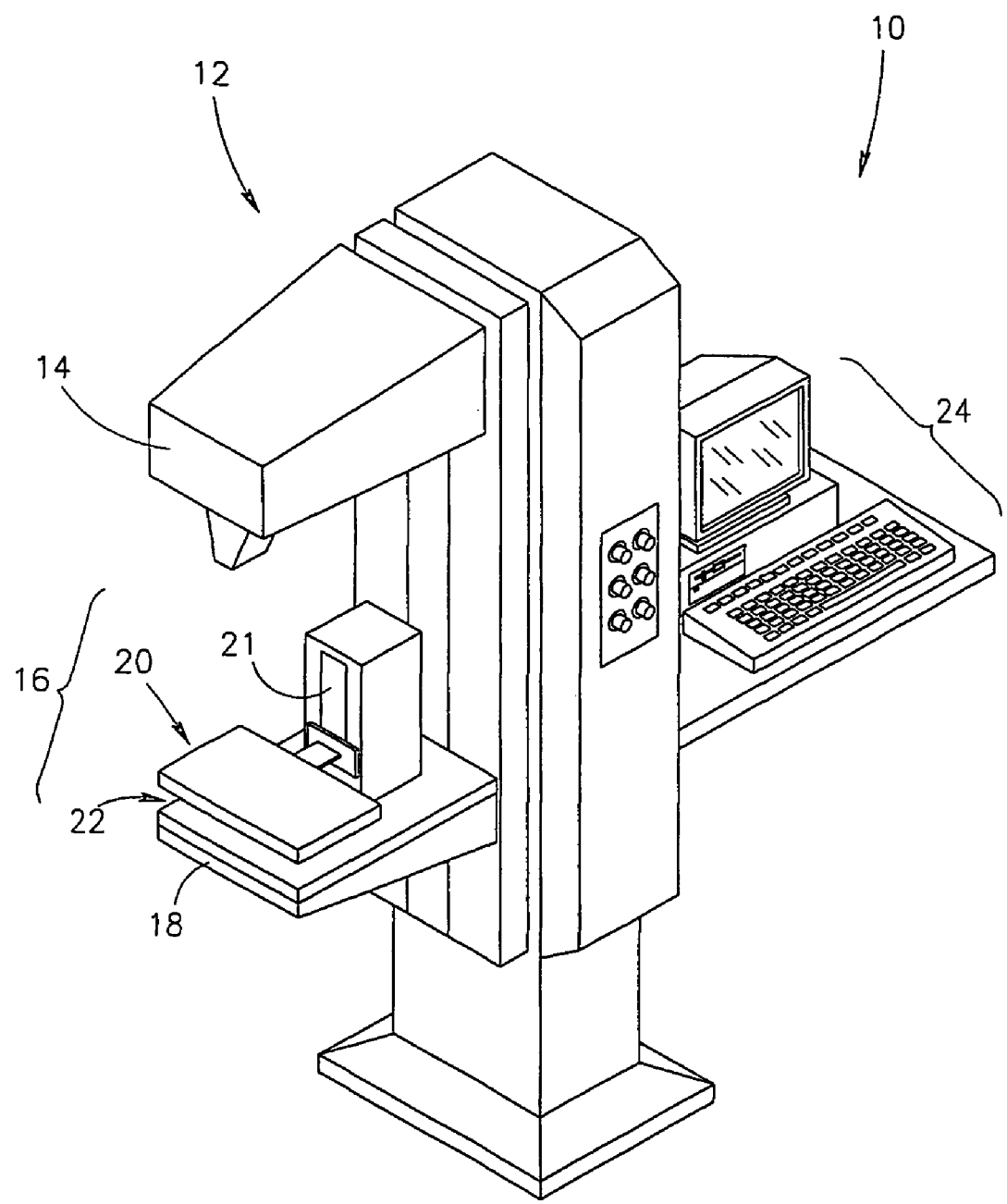
FIG. 1 is a schematic illustration of mammogram, as known in the art.
Figure 2:
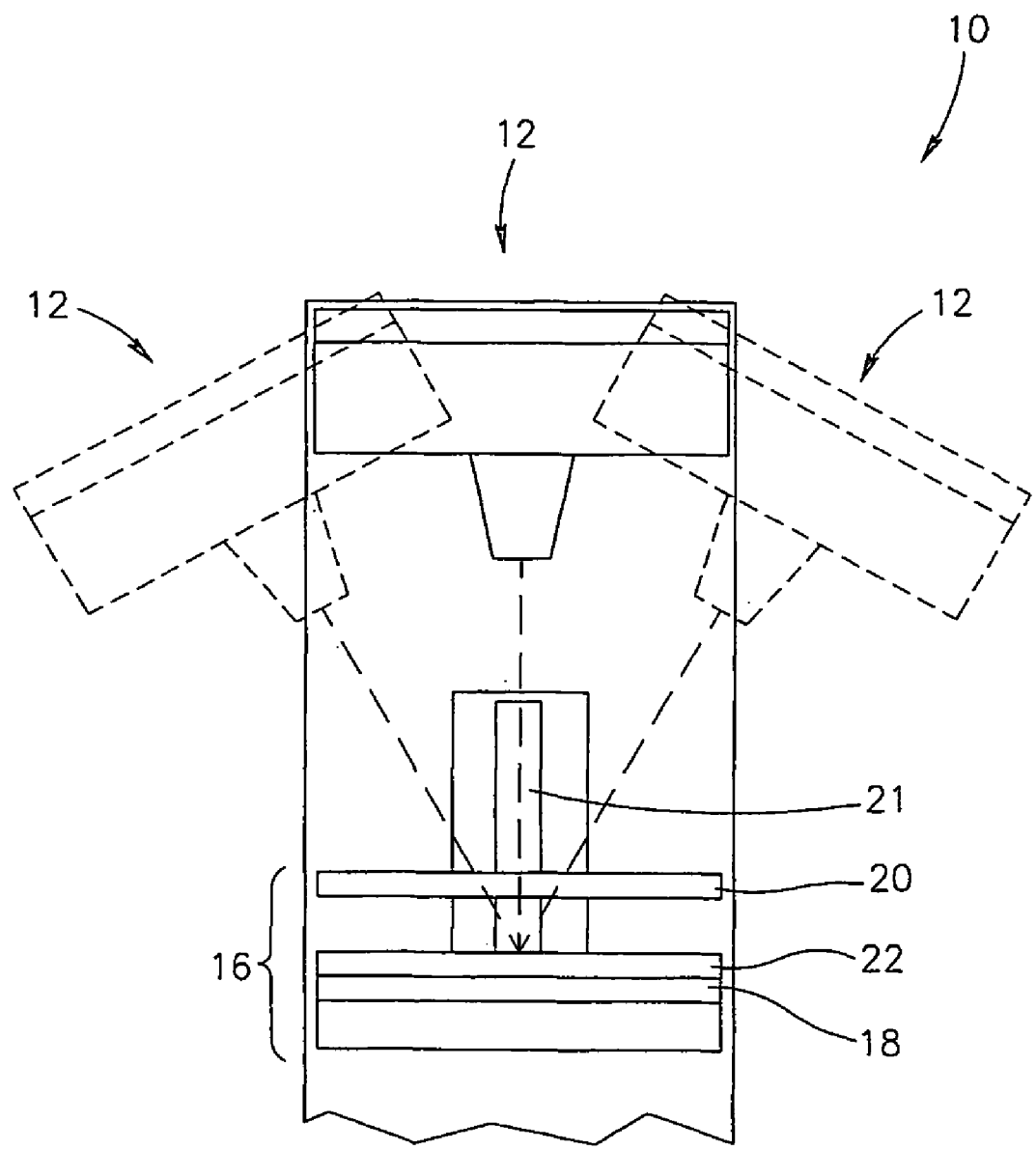
FIG. 2 is a schematic illustration of stereoscopic mammography, as known in the art.
Figure 3A:
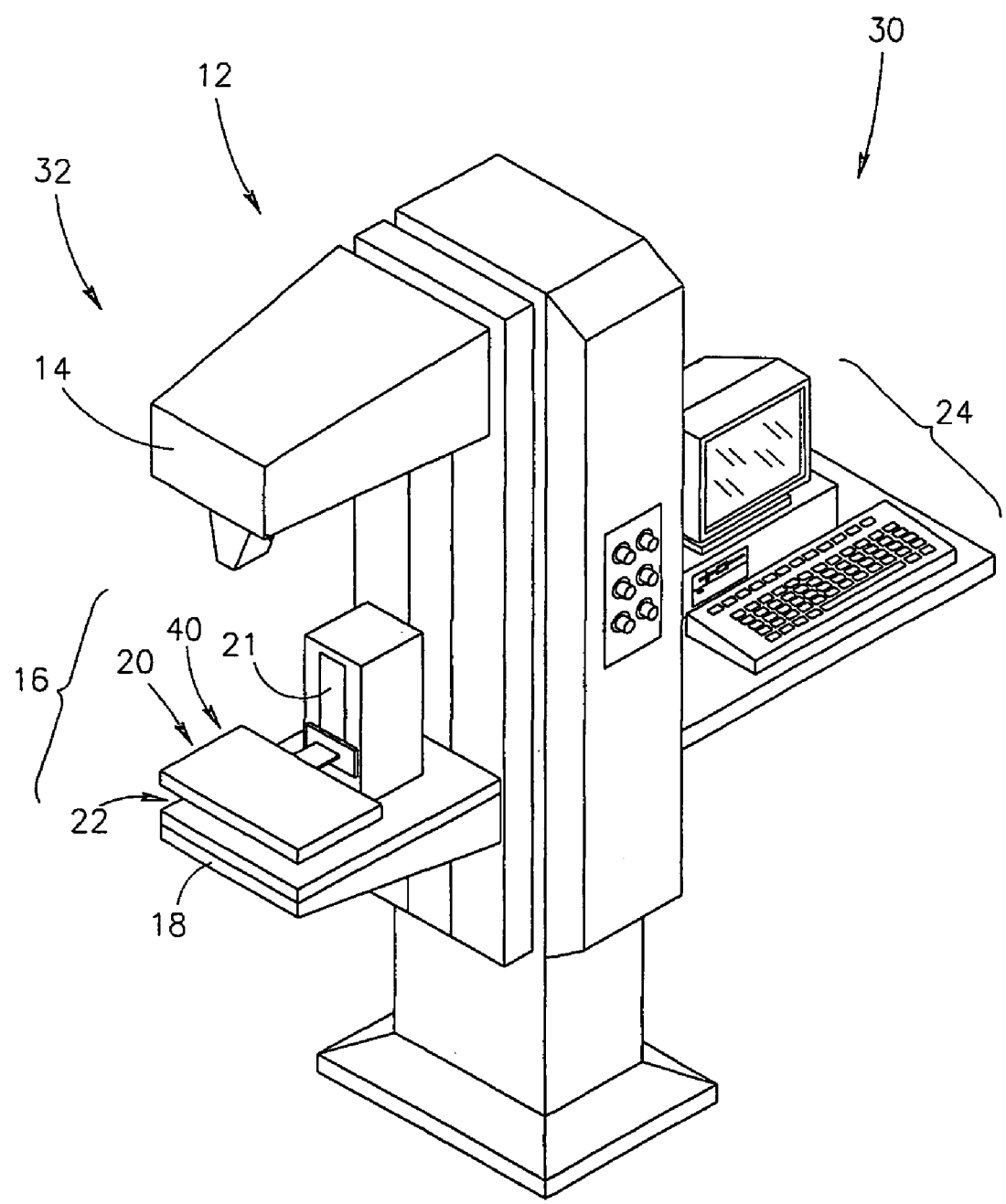
FIGS. 3A and 3B are schematic illustrations of dual-purpose apparatus for mammography and impedance-imaging, in accordance with an embodiment of the present invention.

Reference is now made to FIG. 3A, which is a schematic illustration of dual-purpose apparatus 30 for mammography and impedance-imaging, in accordance with an embodiment of the present invention. As shown, dual-purpose apparatus 30 comprises mammogram 32, which includes a head 12, an x-ray tube 14, a base 16, a compression plate 20 adapted to travel, for example, on a gantry 21, a support plate 22, an image receptor 18 (which may be digital) and optionally, a computer 24. Dual-purpose apparatus 30 generally further comprises at least one impedance probe 40. Optionally, impedance probe 40 is a multi-element impedance probe.

In some embodiments of the invention, dual-purpose apparatus 30 comprises, in a permanent configuration, x-ray apparatus 32 and at least one impedance probe 40. For example, at least one impedance probe 40 may be comprised in either compression plate 20 as illustrated in FIG. 3A, and/or in support plate 22. In FIG. 3A, impedance probe 40 itself serves as compression plate 40. In this configuration, impedance probe 40 may be strengthened with a stiff PVC board, or another preferably radiolucent, stiff material.

In other embodiments of the invention, dual-purpose apparatus 30 is a modular apparatus comprising x-ray apparatus 32 as one module, and at least one impedance probe 40 as another module, wherein the modular apparatus can operate with only one of either modules or with both. The two modules, the x-ray and impedance imaging apparatus may be attached mechanically, in a manner that provides precise and repeatable alignment. Impedance probe 40 may be attached to the tissue side of compression plate 20, as illustrated schematically in FIG. 3B, described below. Similarly, in an alternate or additional configuration, impedance probe 40 may be attached to the tissue side of support plate 22.

Figure 3B:
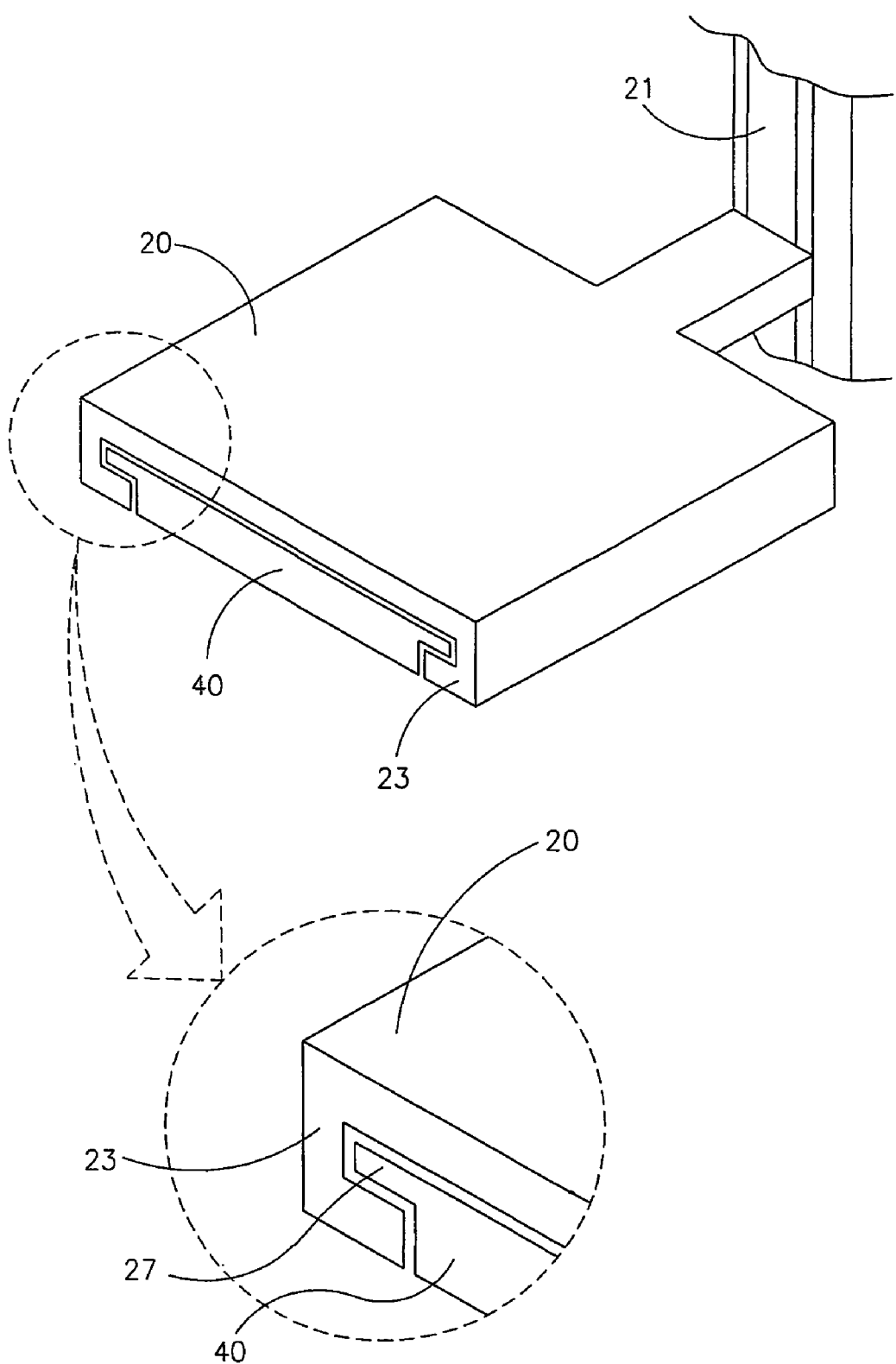

FIG. 3B illustrates a tongue in grove arrangement of mechanically attaching and aligning the x-ray and impedance modules. Compression plate 20 and impedance probe 40 may be substantially of the same width. Compression plate 20 may be formed with grooved rims 23 along at least two (preferably parallel) edges, and impedance probe 40 may be formed with at least two (preferably parallel) tongues 27, wherein impedance probe 40 is adapted to slide in and out of position, with tongues 27 fitting into grooved rims 23. In some embodiments, grooved rims 23 are on the portion of compression plate 20 that does not abut the chest of the patient, even when impedance probe 40 is not in use.

Figure 3C:
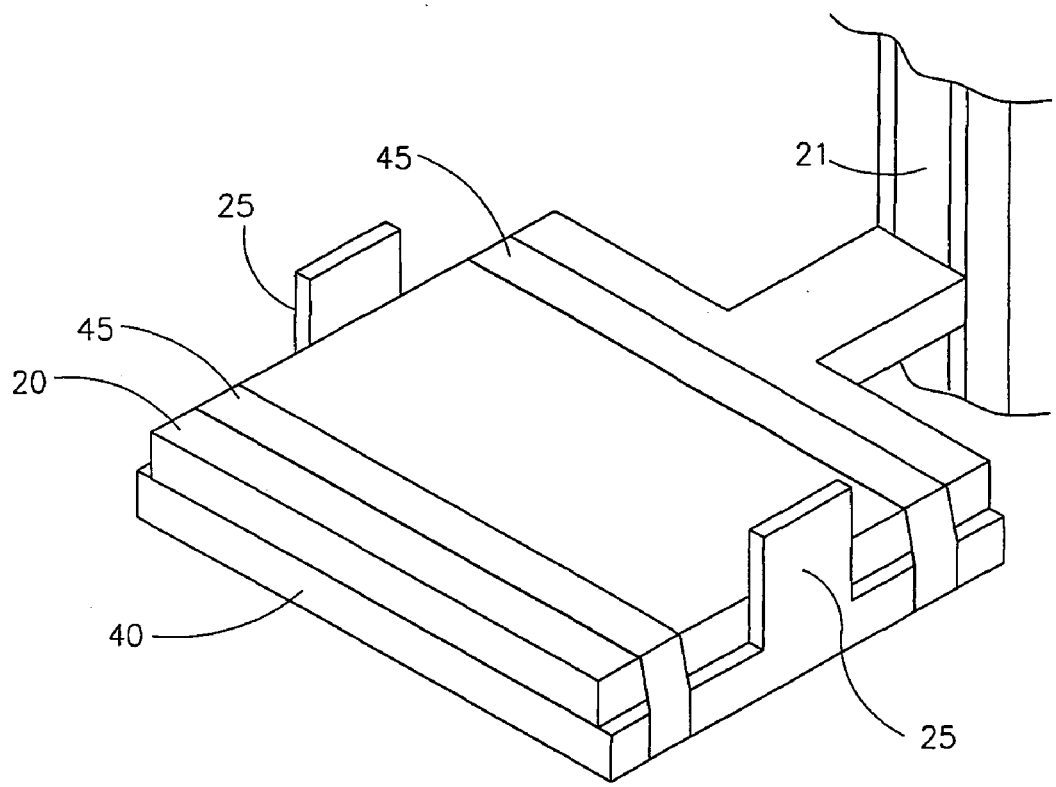
FIGS. 3C and 3D are schematic illustrations of alternative manners of attaching an impedance probe to a compression plate, in accordance with some embodiments of the present invention.

In other embodiments of the invention, impedance probe 40 is constructed as an add-on unit that can be mounted on existing x-ray apparatus available in the market (in a manner that provides precise, repeatable alignment between the two imaging apparatus), but can also operate alone. For example, as illustrated in FIG. 3C, impedance probe 40 is attached to compression plate 20 with straps, while compression plate 20 is aligned against at least two rims 25 along portions of at least two edges of impedance probe 40. Optionally, at least two rims 25 are parallel. Alternatively, they form at least one corner. Optionally, compression plate 20 is sized so as to fit within at least two rims 25. Optionally, at least two rims 25 do not abut the tissue.

Figure 3D:
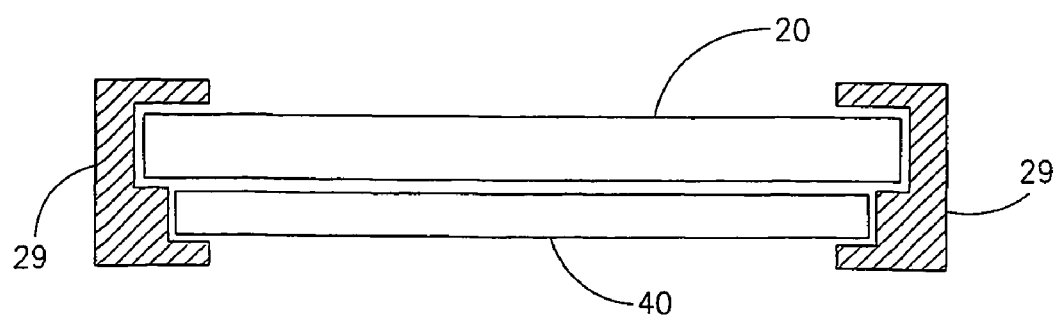

In still other embodiments of the invention, both the x-ray and the imaging apparatus are standard imaging apparatus, available in the market, and they are attached and aligned with each other with a special fixture constructed for that purpose, in a manner that provides precise, repeatable alignment between the two imaging apparatus. This configuration is illustrated in FIG. 3D, where two special, tight-fit brackets 29 are used to mount and align impedance probe 40 with a plate, for example, compression plate 20. Note that the design of bracket 29 may be such as to allow impedance probe 40 and the x-ray plate to be of different widths. Optimally, brackets 29 are on the sides that do not abut the tissue.

Other mechanical devices may be advantageously used for attaching and aligning the two imaging apparatus. For example, male-female snaps, screws or nuts and bolts, adhesives or Velcro fasteners may be used. Precise, repeatable alignment of multi-element probe 40 with compression plate 20 and or support plate 22 may be achieved even with a felt-tip marker.

Figure 4A:
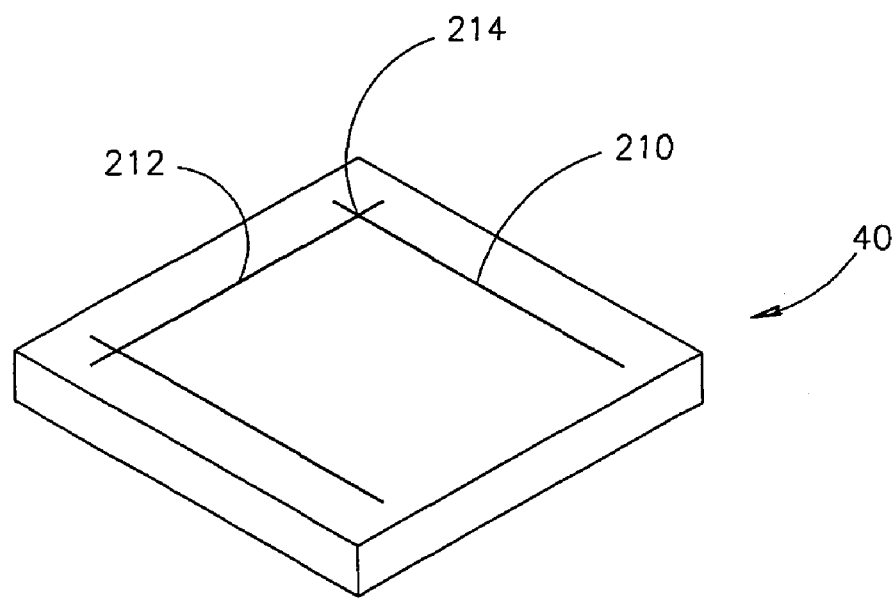
FIGS. 4A and 4B are schematic illustrations of alignment marks associated with the multi-element impedance probe, in accordance with some embodiments of the present invention.
Figure 4B:
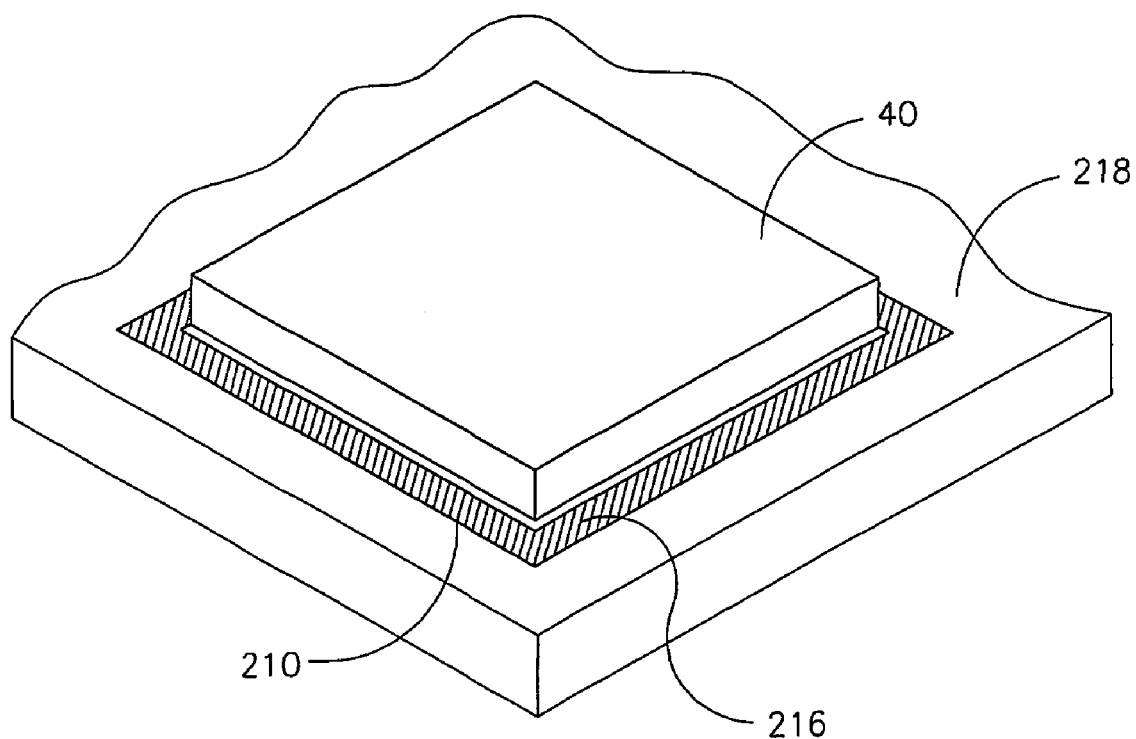

In some embodiments of the invention, alignment between the two imaging apparatus is achieved with lines of x-ray absorbing material deposited on impedance probe 40, in the field of view of x-ray imaging apparatus 32, so that they appear on the x-ray image, as illustrated in FIGS. 4A and 4B. These lines may be outside the cross-sectional area of the tissue of interest. Alternatively, the lines may be inside the cross-sectional area of the tissue, and may be removed by image processing.

Reference is now made to FIG. 4A which is a schematic illustration of multi-element impedance probe 40 comprising an x-ray absorbing (non-radiolucent) alignment mark 210 on otherwise radiolucent or partially radiolucent impedance probe 40. Alignment mark 210 may be formed of a material that is sufficiently absorbing to show on the x-ray image, but not so absorbing that it can cause artifacts, for example, it is formed of aluminum. Alignment mark 210 may comprise at least two or three lines 212. Lines 212 may be arranged so as to provide at least one and preferably two junctions 214. Lines 212 and junctions 214 may be visible. Alternatively or additionally, their locations on impedance probe 40 may be known. Lines 212 may be a substantial distance apart with respect to the size of impedance probe 40. X-ray imaging may be performed with impedance probe 40 in place.

Reference is now made to FIG. 4B which is a schematic illustration of an alignment mark 210 associated with multi-element impedance probe 40, but not on it. Alignment mark 210 may be comprised in a partial or complete outline 216 of multi-element impedance probe 40 on a surface 218 against which multi-element impedance probe 40 is positioned. Surface 218 may be a tissue surface, or a structural surface such as a surface of an examination table or a surface of a support plate. Alternatively, outline 216, in which alignment mark 210 is comprised, is a detachable mount that frames and aligns multi-element impedance probe 40.

When impedance probe 40 comprises alignment mark 210, it may be placed on support plate 22 of a vertical mammogram 32 with no attachment fixtures.

In some embodiments of the invention, as will be seen in the following discussion, radiolucent impedance probe 40 may be used together with gamma scanning, SPECT, or PET. Alignment mark 210 may then be of a material that emits γ rays, or of a material that emits pairs of positrons, rather than of an x-ray absorbing material. Alternatively still, alignment mark 210 comprises a combination of any of an x-ray absorbing material, a material that emits γ rays, and of a material that emits pairs of positrons, in order to be visible on several modalities.

Reference is now made to FIGS. 5A and 5B which are schematic illustrations of multi-element impedance probe 40, showing a side view and a top view respectively, in accordance with an embodiment of the present invention. Optionally, multi-element impedance probe 40 comprises a raster of sensors 43 and associated wiring on a substrate 46, for example, raster of sensors 43 comprises a grid of conductive electrodes. Alternatively, raster of sensors 43 comprises elongated strips of conductors, arranged in parallel rows. Alternatively, raster of sensors 43 comprises some other pattern. Raster of sensors 43 and associated wiring 44 may be attached to a cable 50 via an appropriate connecting element such as an edge connector 48. Cable 50 may connect, for example, to an electrical impedance scanning device (not shown), for example, via a connector 52. The electrical impedance scanning device may be a T-Scan™ 2000 Impedance Scanner of TransScan, Israel. Alternatively, the electrical impedance scanning device may be any other electrical impedance scanning device, as known in the art, such as that described in the above referenced U.S. Pat. Nos. 5,810,742, 4,458,694, PCT application PCT/IL00/00127 or U.S. patent application Ser. No. 09/460,699, now U.S. Pat. No. 6,560,480. The electrical impedance scanning device generates an output that is fed to computer 24.

In some embodiments of the invention, multi-element impedance probe 40 is radiolucent and does not to interfere with the x-ray imaging. The raster of sensors and associated wiring 44 may be made of radiolucent, conductive materials such as a graphite-based deposit or a thin layer of silver-based deposit. Substrate 46 may be made of a radiolucent, nonconductive material such as plastic (for example, mylar®, polycarbonate, PVC, or Tyvec®) or paper and may be hypoallergenic and otherwise biocompatible. Optimally, multi-element impedance probe 40 is completely transparent to x-rays. Alternatively, multi-element impedance probe 40 is substantially transparent to x-rays, causing only minimal shadowing. Thus, x-ray imaging may be performed with multi-element impedance probe 40 in place, causing little or no interference to the x-ray image.

In some embodiments of the invention wherein x-ray apparatus 32 is digital imaging apparatus, multi-element impedance probe 40 may be only partially transparent to x-rays. While x-ray imaging is performed with multi-element impedance probe 40 in place, computer 24 utilizes a signal processing program to remove the anticipated pattern of multi-element impedance probe 40. Shadowing can be removed by post processing using image processing of any known type.

In exemplary embodiments of the invention, the process for obtaining x-ray images and impedance images of a woman's breast, using dual-purpose apparatus 30, comprises the following steps:

1. The patient lays her breast (not shown) on support plate 22. Compression plate 20, onto which radiolucent, multi-element impedance probe 40 is attached, is brought down for firm compression of the breast.
2. An x-ray image is obtained.
3. An impedance image is obtained, while the breast is maintained under compression at stationary base 16.

Note that the x-ray image and impedance image may be obtained in any order. Alternatively, they are obtained simultaneously.

The entire process may be repeated for a different angular view, for example, a lateral view, in which the apparatus is rotated, and the breast is compressed from the side. Since the breast is maintained under compression throughout the associated procedures of x-ray imaging and impedance imaging, the x-ray image and the impedance image have the same coordinate system, or the same reference indicator. Consequently, the x-ray image and the impedance image can be compared against each other and agreement between the two procedures can be sought.

In some embodiments, both the x-ray apparatus and the impedance probe produce a digital image that can be overlaid and viewed on a computer monitor. Alternatively, film images of the two techniques are produced and superimposed on a light box. Alternatively, a computer image is printed on a transparency for viewing with a film image, on a light box. Alternatively still, a film image is scanned in order to produce a digital image, and the digital images are overlaid and viewed on a computer monitor.

In some embodiments of the invention, digital images that are overlaid and viewed on the computer monitor can undergo image processing by the computer. Image processing may comprise changing the dimensions of one image, in order to match the dimensions of the other image; zooming in on an area, removing noise of any kind and other image-enhancement processing as known in the art.

In some embodiments of the invention, a symbiotic relationship takes place. Since each technique relies on different properties of the lesion, impedance imaging enhances the understanding of x-ray imaging and vice versa. In general, coincident detection of features is expected. When anomalies are seen only on one modality, settings and methods may be somewhat altered in order to arrive at coincident detection, wherein the knowledge of the improved settings and methods may be used in future imaging.

In some embodiments, the symbiotic relationship is further extended to the understanding of what features and types of lesions are better visualized by x-ray, and what features and what types of lesions are better detected by impedance. As such, specificity and sensitivity of each technique to certain features and types of lesions may be studied and compared. Since different sensitivities exist, the use of both modalities together allows for more through diagnosis.

Figure 6A:
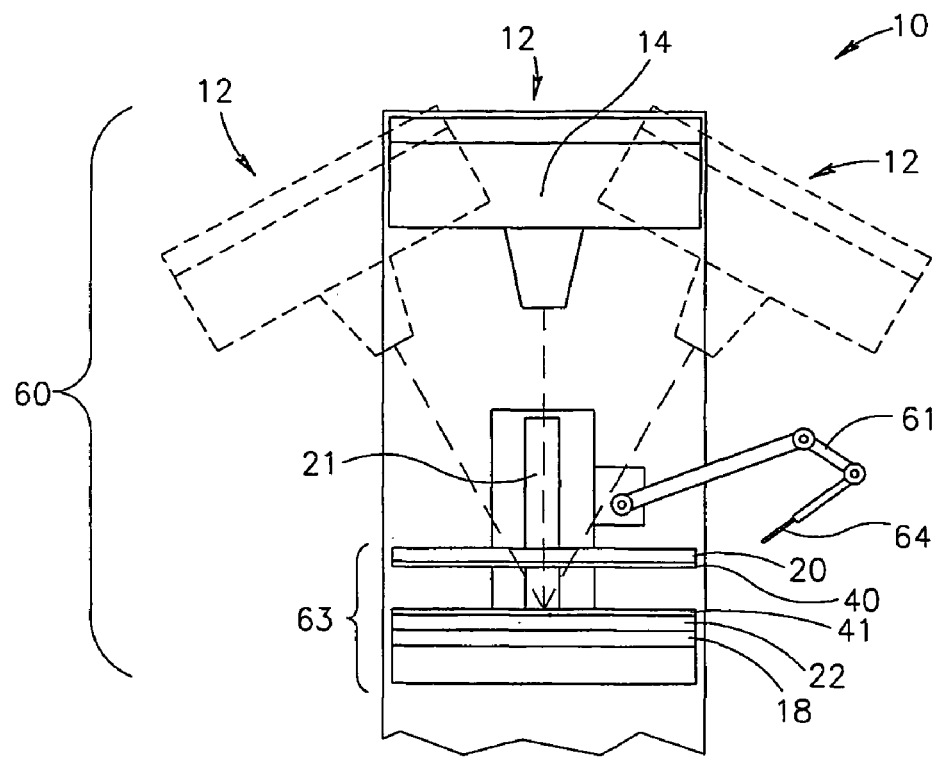
FIG. 6A is a schematic illustration of multi-purpose apparatus for mammography, impedance-imaging and biopsy core sampling, in accordance with an embodiment of the present invention.
Figure 6B:
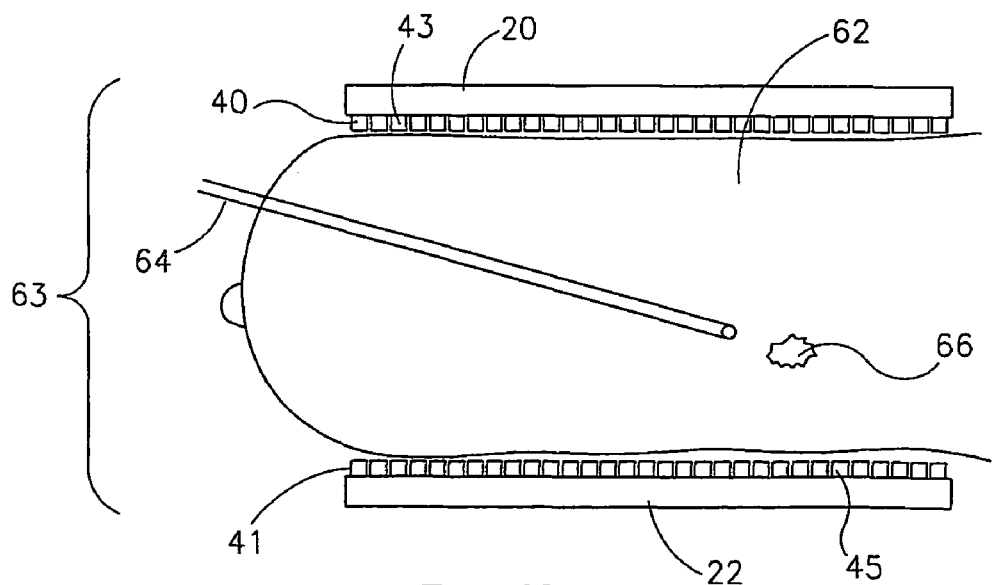
FIG. 6B is an enlarged view of a breast-holding section and a biopsy core needle, in accordance with an embodiment of the present invention.

Reference is now made to FIGS. 6A and 6B which are schematic illustrations of dual-purpose apparatus 30 which comprises two identical multi-element impedance probes 40 and 41, in accordance with an embodiment of the present invention. As shown, multi-element impedance probe 40, having raster of sensors 43, acts as a source electrode. Identical multi-element impedance probe 41, having raster of sensors 45, acts as a sensor. Thus, a separate reference electrode need not be used. Alternatively, the two impedance probes alternate as source and sensor. In the embodiment shown in FIGS. 6A and 6B, multi-element impedance probe 40 is placed on the tissue side of compression plate 20 and multi-element impedance probe 41 is placed on the tissue side of support plate 22. A known signal is applied to one probe, while the sensors of the other probe measure the resulting current (or voltage) across the tissue. As before, the resulting current (or voltage) is fed to the electrical impedance scanning device which generates an output that is fed to computer 24.

In some embodiments, each sensing element of raster of sensors 43 and (or) 45 is controlled separately such that at any single moment some of raster of sensors 43 and (or) 45 may measure signals, others may provide excitation, and still others may be passive. In some embodiments, elements of raster of sensors 43 and (or) 45 which provide excitation may be driven separately, such that at a single moment different elements of raster of sensors 43 and (or) 45 provide signals at different amplitudes, frequencies and (or) relative phases. Alternatively or additionally, groups of elements of raster of sensors 43 and (or) 45, forming predetermined shapes on multi-element impedance probe 40, may be driven together.

In some embodiments of the invention, dual-purpose apparatus 30 comprises two different impedance probes, one acting as a source and the other as a sensor (wherein a separate reference electrode is preferably not used). The sensor probe may be a multi-element impedance probe 40, described in FIGS. 5A and 5B, while the source may be simpler in construction and may comprise a planar conductive electrode. Alternatively, the source probe may comprise elongated strips of conductors arranged in a parallel rows. Alternatively, the source probe may comprise some other pattern of conductors. Such probes and their operation is described in more detail in the above referenced Patents and PCT applications.

Reference continues to be made to FIG. 6A, which is a schematic illustration of multi-purpose apparatus 60 for stereoscopic mammography, impedance-imaging and biopsy core sampling, using a single reference indicator, in accordance with an embodiment of the present invention. Reference is now also made to FIG. 6B which is a schematic illustration of a breast holding section 63 of apparatus 60, in accordance with an embodiment of the present invention. In cases where a lesion is observed by impedance imaging but not by x-ray imaging, the complete information regarding a 3-D location of the suspected lesion can be obtained from impedance imaging alone. Optimally, the entire breast is in the field of view of the impedance imager.

Exemplary embodiments of multi-purpose apparatus 60 comprise:
  head 12 comprising x-ray tube 14, mounted on a gantry that turns on an arc;
  compression plate 20 adapted to travel in a linear motion;
  support plate 22;
  x-ray image receptor 18 (which may be digital);
  computer 24 (not shown);
  a biopsy needle 64, held by a secondary gantry 61;
  multi-element impedance probe 40, comprising raster of sensors 43; and
  multi-element impedance probe 41, comprising raster of sensors 45.

Sensing element of raster of sensors 43 and 45 may be identical and may be controlled separately.

In accordance with an embodiment of the invention, the x-ray and impedance images are aligned mechanically or with an alignment mark 210. Alternatively, they can be integrated into a single unit.

Depth estimation, for guiding a biopsy needle, using impedance imaging is described in the specification of the above referenced U.S. patent application Ser. No. 09/460,699, now U.S. Pat. No. 6,560,480, the disclosure of which is incorporated herein by reference, and delineated here for multi-purpose apparatus 60 for mammography, impedance-imaging and biopsy core sampling.

Figure 7C:
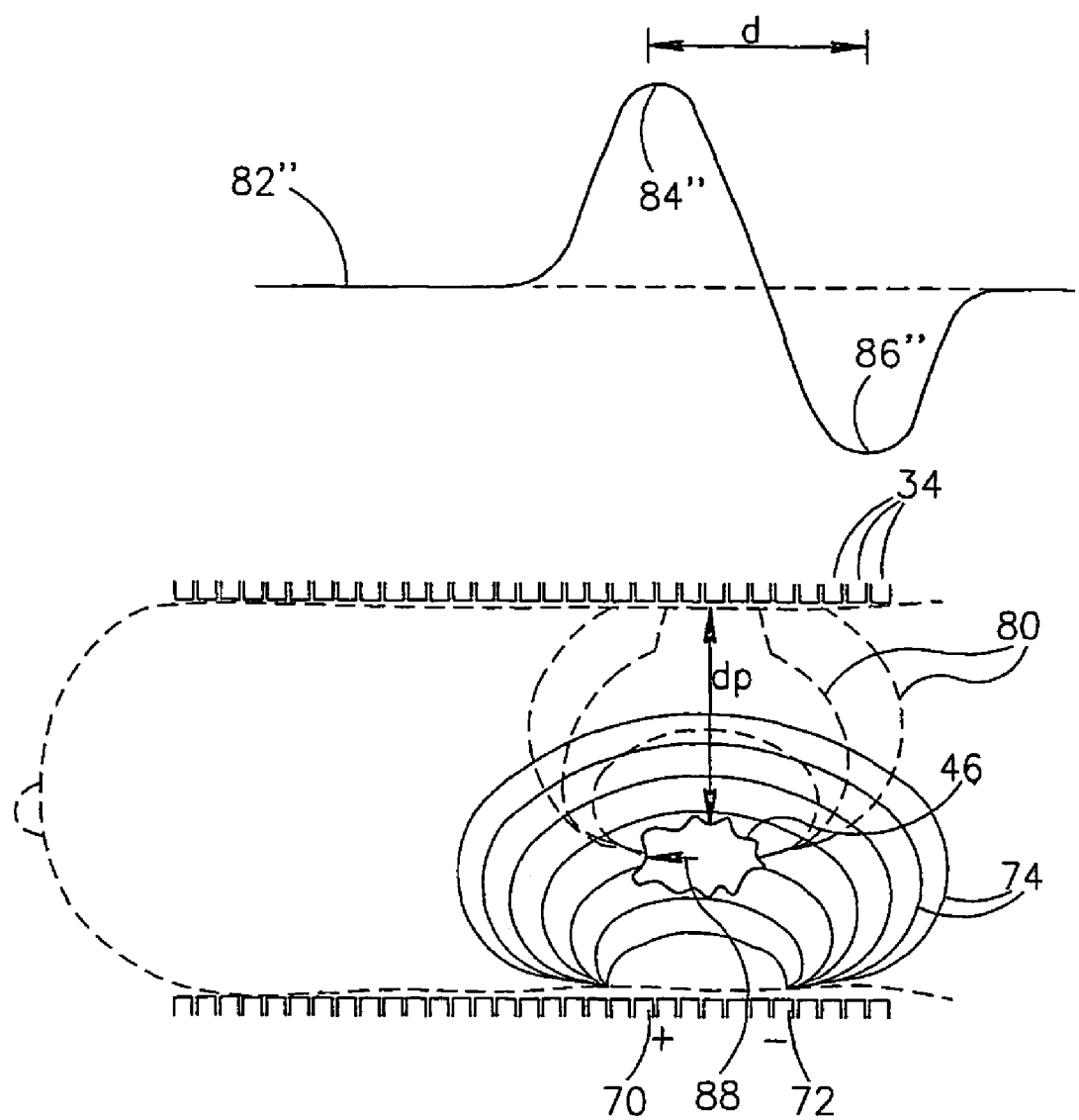

Reference is now made to FIGS. 7A–7C which schematically illustrate a method of depth determination using multi purpose apparatus 60, in accordance with an embodiment of the present invention and as described in the referenced US application.

As shown in FIG. 7A and described therein, raster of sensors 45 of multi-element impedance probe 41 may be used to form an excitation dipole. For example, a positive voltage signal is applied to a line 70 (into the paper) of raster of sensors 45. A negative voltage signal of opposite polarity may be applied to a line 72 of raster of sensors 45 parallel to line 70. The dipole formed by lines 70 and 72 generates an electrical field schematically illustrated by lines 74. The electrical field preferably induces a counter dipole within anomaly 66, as indicated by arrow 78. The direction of the counter dipole is a function of the distance between anomaly 66 and lines 70 and 72. As shown in FIG. 7A, when the dipole of lines 70 and 72 is far away from anomaly 66, the direction of the counter dipole is substantially from impedance probe 41 to impedance probe 40. The counter dipole induces within a breast 62 an electrical field indicated by dashed lines 80.

In an embodiment of the invention, sensors 43 on impedance probe 40 are held at a virtual ground. Therefore, only currents perpendicular to impedance probe 40 are registered by sensors 43. The influence of the dipole within anomaly 66 on the array of sensors 43 is shown schematically by a line 82. Line 82 is a cross section of the map formed by sensors 43 taken above anomaly 66. Line 82 is arrived at by subtracting the direct influence of current from lines 70 and 72 from the signals sensed by sensors 43. (However, it is noted that the direct current from lines 70 and 72 decreases in proportion to the square of the distance and therefore interferes to a lesser extent in determining the current from anomaly 66 than current from a single positive line 70 without applying the negative voltage signal of opposite polarity is to line 72). Line 82 includes a single peak 84 above anomaly 66. The height of peak 84 depends on the location and characteristics of anomaly 66.

FIG. 7B is a schematic illustration of an imaging stage in which lines 70 and 72 are relatively close to anomaly 66. As the dipole formed of lines 70 and 72 approaches anomaly 66, the counter dipole within the anomaly forms an angle relative to impedance probes 40 and 41. Accordingly, field lines 80 also form an angle relative to impedance probes 40 and 41. The influence of the dipole within anomaly 66 on the array of sensors 43 is shown schematically by a line 82' in a manner similar to line 82 of FIG. 7A. In addition to peak 84' as in line 82, line 82' has a negative peak 86'. As lines 70 and 72 approach anomaly 66 the height of peak 84' is reduced while peak 86' is increased.

It is noted that peaks 84' and 86' do not run along the entire length of impedance probe 40 (into the paper) but are limited to the position of anomaly 66.

FIG. 7C is a schematic illustration of an imaging stage in which anomaly 66 is located between lines 70 and 72. As shown in FIG. 7C, when anomaly 66 is between lines 70 and 72 the counter dipole within anomaly 66 is substantially perpendicular to lines 70 and 72, as indicated by an arrow 88. When anomaly 66 is substantially in the center between lines 70 and 72, peaks 84" and 86" of line 82" are of substantially equal height. The distance d between peaks 84" and 86" is a function of the depth dp of anomaly 66 in breast 62, and of the size of anomaly 66.

It is thus possible to use impedance imaging alone for 3-D location determination of an anomaly. Other methods of determining a 3-D location of a lesion are also described in the US application.

Figure 8:
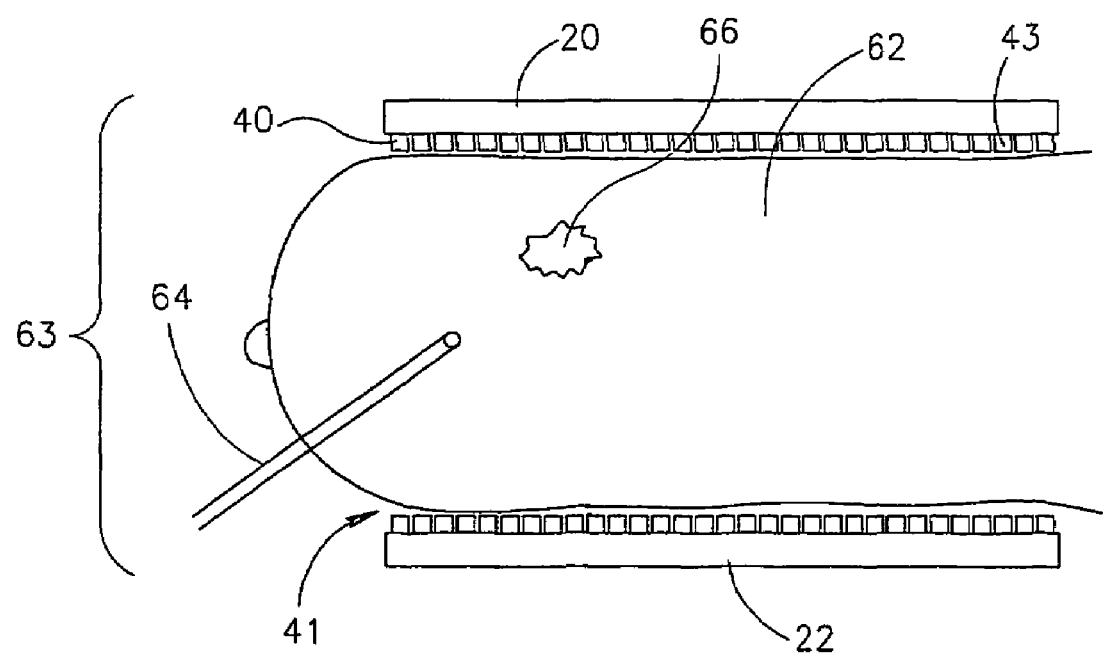
FIG. 8 is a schematic illustration of impedance-guided biopsy, in accordance with an embodiment of the present invention.

Reference is now made to FIG. 8, which is a schematic illustration of impedance-guided biopsy, in accordance with still another embodiment of the present invention, as is also described in the US application. Preferably, biopsy needle 64 is made of a conducting material, and wired as an impedance source. In some preferred embodiments, impedance-guided biopsy needle 64 is used in conjunction with a single multi-element impedance probe 40. Alternatively, two multi-element impedance probes may be used.

In this embodiment, as impedance-guided biopsy needle 64 approaches lesion 66, it generates an electrifying signal which are sensed by multi-element impedance probe 40 (and possibly also multi-element impedance probe 41, shown on FIG. 6B). Thus, the image formed by multi-element impedance probe 40 (and possibly also multi-element impedance probe 41) can be used to monitor, manually or automatically, the movements of impedance-guided biopsy needle 64 toward lesion 66. When needle 64 touches or enters the lesion 66, the direct electrification of the lesion by the needle induces a detectable change in the signals due to the lesion, whereupon, a core sample is taken. This method is used as confirmation that the core sample was indeed taken from an anomalous area.

Figure 9:
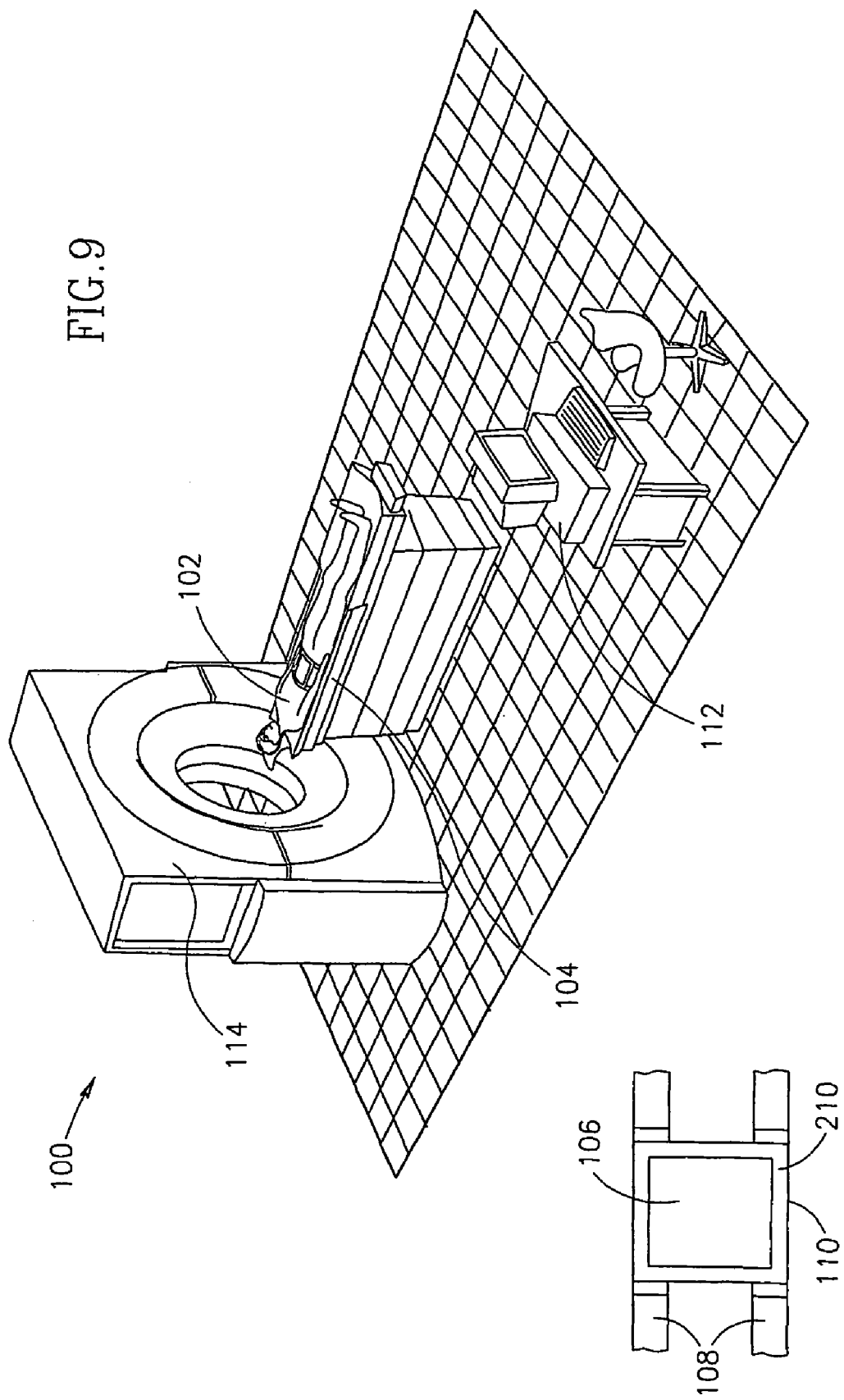
FIG. 9 is a schematic illustration of a dual-purpose system for CT and impedance imaging, in accordance with an embodiment of the present invention.

Reference is now made to FIG. 9, which is a schematic illustration of a dual-purpose system 100 for CT and impedance imaging, in accordance with an embodiment of the invention. Preferably, dual-purpose system 100 comprises a patient table 104, a control console 112, and a gantry 114 that contains the x-ray source, the x-ray detectors and the data acquisition system of the CT system and an impedance probe, preferably a multi-element impedance probe 106.

Generally, a patient 102 lies on CT table 104. Impedance probe 106 may be attached to the patient, for example by straps 108. Impedance imaging is then performed. Optionally, multi-element impedance probe 106 is radiolucent and mounted on a frame 110 of an x-ray absorbing material, in which alignment mark 210 is comprised. Optimally, alignment mark 210 is of a material that is sufficiently absorbing to show on the x-ray image, but not so absorbing that it can cause artifacts, for example, thin aluminum. CT measurements can be performed with the radiolucent impedance probe in place. In this manner, an outline of the 2-D impedance probe is produced on the CT image, and comparison of the two images is possible. Alternatively, frame 110 is not used, and radiolucent impedance probe 106 comprises x-ray absorbing alignment mark 210 shown in FIGS. 4A and 4B.

Alternatively, impedance probe 106 is not radiolucent and comprises any known impedance probe that has been fitted with a detachable frame 110 of x-ray absorbing material. Frame 110 is attached to patient 102, using straps 108, and impedance probe 106 is inserted into it. Impedance imaging is performed. Impedance probe 106 is then removed from detachable frame 110, which remains attached to patient 102 for defining the field of view of the impedance image on the CT image. Frame 110 comprises at least one, two or more strips of x-ray absorbing material, optionally placed perpendicular to the CT beam. Optionally, frame 110 further comprises at least one and preferably two crosses, optimally outside the tissue area of interest. In some embodiments, frame 110 is similar in construction to alignment mark 210 of FIG. 4B. Straps 108 are optimally outside the field of view of the CT. In some embodiments, a thin, rigid plate of uniform, radiolucent material (not shown) is inserted into frame 110 when impedance probe 40 is removed, to give the same tissue-pressing effect for the CT imaging as occurred for the impedance imaging.

It should be noted that while the invention is described herein in conjunction with x-ray mammography, the present invention is also applicable to nuclear imaging, such as SPECT, and PET. In these cases gantry 114 symbolically represents the gamma imagers. In some embodiments radioactive alignment mark 210 shown in FIGS. 4A and 4B, comprising a material that emits γ rays or a material that emits pairs of positrons may be used. Radioactive alignment mark 210 makes it possible to superimpose the impedance image on the SPECT or PET image, and seek agreement between the results.

Figure 10:
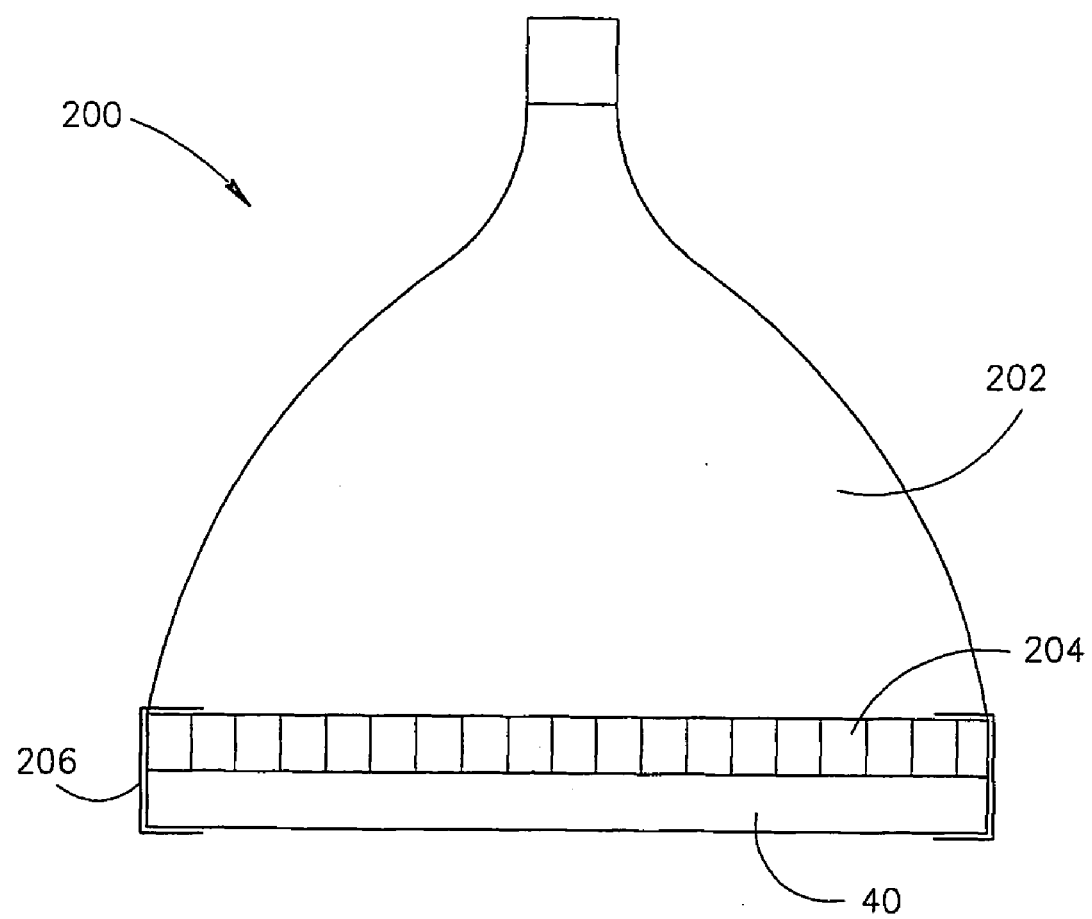
FIG. 10 is a schematic illustration of a dual-purpose system for gamma scanning and impedance imaging, in accordance with an embodiment of the present invention.

Reference is now made to FIG. 10 which is a schematic representation of a dual-purpose machine 200 comprising a hand-held gamma camera 202 and multi-element impedance probe 40, in accordance with an embodiment of the invention. Gamma camera 202 may comprise a fixed mechanical attachment 206 which holds impedance probe 40 in place. Optimally, multi-element impedance probe 40 is radiolucent. In some embodiments, fixed mechanical attachment 206 is used to hold multi-element impedance probe 40 at a specific location with respect to a collimator 204 of gamma camera 202. For example, multi-element impedance probe 40 may be attached to gamma camera 202 directly in the frame of view of camera 202, at a specific distance, much like an infrared screen is attached to a regular camera.

A triple-purpose machine comprising a mammogram 32, an impedance probe 40 and a gamma camera 200, is also possible, wherein impedance probe 40 is comprised in compression plate 20 of mammogram 32 and gamma camera 200 fits onto impedance probe 40-compression plate 20, with mechanical attachment 206.

Since the mechanical alignment between gamma camera 202 and multi-element impedance probe 40 is fixed, it is possible to superimpose the impedance image on the nuclear image and seek agreement between the results. Alternatively, radioactive alignment mark 210 shown in FIGS. 4A and 4B, comprising a material that emits γ rays are used, to make superposition of the images possible.

Alternatively, any impedance probe that is known, and which is not radiolucent, may be used. The process of applying nuclear imaging, such as by gamma camera (which may be hand-held), SPECT, or PET, in conjunction with impedance imaging, referenced to the same reference indicator, may comprise the following steps:

1. providing any impedance probe;
2. strapping the impedance probe to the tissue (for example, using straps 108 shown on FIG. 9);
3. obtaining an impedance image;
4. tracing the outline of the impedance probe on the patient's body, with a brush such as a water-color brush, using the radio-pharmaceutical solution that has been administered to the patient as ink;
5. removing the impedance probe; and
6. applying a desired nuclear imaging technique.

In this manner, an outline of the 2-D impedance probe is produced on the nuclear image.

In some embodiments, a thin, rigid plate of uniform, radiolucent material is strapped to the tissue when the impedance probe is removed, to give the same tissue-pressing effect for the nuclear imaging as occurred for the impedance imaging.

It should be noted that while it is desirable, in many cases, to align the coordinate systems of the impedance image and the other image using some external means such as alignment marks or mechanical means, such means are not absolutely necessary. In general, it will be possible to align the images by overlaying them and matching characteristic structures in both images, such as the edge of the breast.

In some embodiments of the invention, an interface sheet, interfacing between the tissue and the impedance probe, is used. Preferably, the interface sheet is transparent or partially transparent to x-rays, so as to cause little interference to x-ray imaging. The purpose of the interface sheet may be to provide a hypoallergenic and bio-compatible interface that will cause no irritation to the tissue. Preferably, the interface sheet is also sterile, whereas the unprotected impedance probe that comes in contact with tissue of many individuals. Preferably, the interface sheet is a relatively thin layer of highly hydrolyzed gel or water containing material such as a hydrogel. Such materials may contain between 70% and 95% of water, by weight; therefore, they have a conductivity comparable to that of the tissue. In a sense, they provide an interface which could be considered as merely an extension of the tissue. Thus they provide an interface with no distortion of the fields used to determine impedance or cross-talk other than would be provided by an extra, thin layer of tissue. Preferably, the hydrogel interface sheet provides good wetting of the tissue, thereby eliminating the need to spread gel over the tissue, and eliminating the unpleasantness to the patient, associated with the gel.

In some embodiments of the invention, multi-element impedance probe 40 is a disposable multi-element impedance probe such as that described in U.S. Pat. No. 5,810,742, "Tissue Characterization Based on Impedance Images and on Impedance Measurements," the disclosure of which is incorporated herein by reference and the methods described therein are used to acquire the image.

In some embodiments of the invention, mammogram 32 is a LORAD® M-IV mammogram (manufactured by LORAD, a subsidiary of Trex Medical Corporation, Danbury, Conn.) which includes a cellular grid system for contrast and visual enhancement. Alternatively, mammogram 32 may be any mammogram, as known in the art.

In some embodiments of the invention, mammogram 32 has stereoscopic capability for obtaining x-ray images from at least two viewing angles. Mammogram 32 may be upright for use with sitting or standing patients. Optionally, mammogram 32 can be rotated along the horizontal axis so as to obtain x-ray measurements at any angle. However, mammogram 32 may have fewer degrees of freedom. Alternatively, mammogram 32 is horizontal for use with prone patients. It should be noted that in general, any mammogram may be fitted in accordance with the present invention.

Furthermore, the invention may be applicable for use with any x-ray apparatus as known in the art, for imaging tissue other than the breast. Any x-ray apparatus may be fitted in accordance with the present invention.

Furthermore, while the impedance probes indicated above are preferred, the impedance probe may be any impedance probe as known in the art.

The present invention has been described using non-limiting detailed descriptions of exemplary embodiments thereof that are provided by way of example and are not intended to limit the scope of the invention. Details shown with respect to one embodiment of the invention, may be used with other embodiments, if suitable for such embodiments. Further, some details of some embodiments are non-essential. Furthermore, while some features of the embodiments are described in terms of particular examples thereof, it should be understood that these features are mere examples of broader classes of features which may be employed. Similarly, some features may be omitted in some preferred embodiments of the invention. Variations of embodiments described will occur to persons of the art. Furthermore, the terms "comprising," "comprise," include," and "including" or the like, shall mean, when used in the claims, "including but not necessarily limited to." The scope of the invention is limited only by the following claims:

What is claimed is:

1. Multi-element impedance probe apparatus, adapted to produce an image of a body tissue, having a structure, comprising:
   a raster of sensors, comprised of a substantially radiolucent, conductive material;
   substantially radiolucent conductive wiring, forming conductive connections with the sensors;
   a substantially radiolucent substrate, on which the sensors are mounted; and
   a non-radiolucent aligning feature.

2. Apparatus according to claim 1, comprising two impedance probes which operate in tandem, one acting as an electrifying source and the other as a sensor.

3. Apparatus according to claim 1, and including a conductive layered structure, covering the raster of the sensors and suitable for providing an interface between the sensors and the tissue.

4. Apparatus according to claim 3, wherein the structure comprises a material having conductivity substantially similar to the conductivity of the tissue.

5. Apparatus according to claim 3, wherein the structure is radiolucent.

6. Apparatus according to claim 1, wherein the aligning feature comprises at least one alignment mark that is opaque to x-rays.

7. Apparatus according to claim 1, wherein the aligning feature comprises at least one alignment mark that emits γ rays.

8. Apparatus according to claim 1, wherein the aligning feature comprises at least one alignment mark that emits pairs of positrons.

9. Apparatus according to claim 1, wherein the aligning feature comprises at least two lines, a substantial distance apart with respect to the size of the impedance probe.

10. Apparatus according to claim 1, wherein the aligning feature comprises at least two intersections, a substantial distance apart with respect to the size of the impedance probe.

11. Apparatus according to claim 1, wherein the aligning feature comprises an outline of the probe painted on a surface against which the impedance probe is positioned.

12. Apparatus according to claim 1, wherein the aligning feature comprises a detachable mount to which the impedance probe is attached during operation thereof.

13. Apparatus for tissue examination comprising:
   an impedance imager comprising at least one impedance probe with a first field of view and adapted to produce an impedance image of a body tissue, referenced to a reference indicator; and
   at least one additional imager of a nuclear imaging modality, having a second field of view, at least partially common to the first field of view, and adapted to produce an image of body tissue, referenced to the reference indicator;
   wherein said reference indicator is comprised in a structure that provides positioning of at least one of the imagers or wherein the impedance imager and the at least one additional imager form an integral unit.

14. Apparatus according to claim 13, wherein the reference indicator is comprised in a structure that provides positioning of at least one of the imagers.

15. Apparatus according to claim 13, wherein the impedance imager and the at least one additional imager form an integral unit.

16. Apparatus according to claim 13, wherein:
the impedance imager is a first module; and
each additional imager is an additional module,
wherein the modules may be used independently or together.

17. Apparatus according to claims 13 and including a processing unit common to the impedance imager and the at least one additional imager for processing the images.

18. Apparatus according to claim 13 and including a display unit common to the impedance imager and the at least one additional imager, wherein the display unit is operative to selectively display each image individually or the images superimposed.

19. Apparatus according to claim 13 and including a control panel common to the impedance imager and the at least one additional imager.

20. Apparatus according to claim 13 and including a biopsy device, adapted to perform biopsy on the tissue.

21. Apparatus according to claim 13, wherein the at least one additional imager comprises a gamma camera.

22. Apparatus according to claim 21, wherein the at least one impedance probe is attached to the gamma camera with a fixed mechanical attachment, in a field of view of the gamma camera, at a specific distance from the gamma camera.

23. Apparatus according to claim 13, wherein the at least one additional imager comprises a SPECT imager.

24. Apparatus according to claim 13, wherein the at least one additional imager comprises a PET imager.

25. Apparatus according to claim 13, wherein the tissue is human tissue.

26. Apparatus for x-ray mammography and impedance imaging, comprising:
an x-ray tube, which produces a beam of x-rays;
a support plate, adapted to support a soft body tissue when it is irradiated by the x-ray tube;
an x-ray image receptor, associated with the support plate and adapted to produce an x-ray image of the tissue, referenced to a reference indicator;
an impedance imager, comprising at least one impedance probe, located between the x-ray tube and the x-ray image receptor, having a field of view that is at least partially common to a field of view 6f the x-ray tube and adapted to produce an image of body tissue, referenced to the reference indicator; and
an impedance imager receptor adapted to receive the impedance imager in a manner which allows the impedance probe to be removed, while the soft body tissue remains substantially in place.

27. Apparatus according to claim 26, and including a compression plate, adapted to travel between the x-ray tube and the support plate and to provide compression against the tissue.

28. Apparatus according to claim 26, wherein the at least one impedance probe is comprised in the compression plate.

29. Apparatus according to claim 28, and including a gamma camera, having a field of view that is at least partially common to a field of view of the at least one impedance probe, wherein the gamma camera is adapted to produce a gamma-ray image of the tissue, referenced to the reference indicator.

* * * * *